(12) United States Patent
Faucher et al.

(10) Patent No.: US 9,867,880 B2
(45) Date of Patent: Jan. 16, 2018

(54) CURED OIL-HYDROGEL BIOMATERIAL COMPOSITIONS FOR CONTROLLED DRUG DELIVERY

(71) Applicant: Atrium Medical Corporation, Hudson, NH (US)

(72) Inventors: Keith M. Faucher, Milford, NH (US); Suzanne Conroy, Dracut, MA (US); Theresa K. Albergo, Nashua, NH (US); Joseph Bienkiewicz, Westford, MA (US)

(73) Assignee: Atrium Medical Corporation, Merrimack, NH (US)

( * ) Notice: Subject to any disclaimer, the term of this patent is extended or adjusted under 35 U.S.C. 154(b) by 0 days.

(21) Appl. No.: 13/843,068

(22) Filed: Mar. 15, 2013

(65) Prior Publication Data

US 2013/0337029 A1   Dec. 19, 2013

Related U.S. Application Data

(60) Provisional application No. 61/659,301, filed on Jun. 13, 2012.

(51) Int. Cl.
| | | |
|---|---|---|
| A61K 47/12 | (2006.01) | |
| A61K 47/22 | (2006.01) | |
| A61L 27/34 | (2006.01) | |
| A61L 27/14 | (2006.01) | |
| A61L 27/54 | (2006.01) | |
| A61L 31/04 | (2006.01) | |
| A61L 31/10 | (2006.01) | |
| A61L 31/16 | (2006.01) | |

(52) U.S. Cl.
CPC ............. *A61K 47/12* (2013.01); *A61K 47/22* (2013.01); *A61L 27/14* (2013.01); *A61L 27/34* (2013.01); *A61L 27/54* (2013.01); *A61L 31/04* (2013.01); *A61L 31/10* (2013.01); *A61L 31/16* (2013.01); *A61L 2300/606* (2013.01)

(58) Field of Classification Search
None
See application file for complete search history.

(56) References Cited

U.S. PATENT DOCUMENTS

| | | |
|---|---|---|
| 1,948,959 A | 2/1934 | Croce |
| 2,368,306 A | 1/1945 | Kiefer et al. |
| 2,403,458 A | 7/1946 | Ransom |
| 2,735,814 A | 2/1956 | Hodson et al. |
| 2,986,540 A | 5/1961 | Posnansky |
| 3,464,413 A | 9/1969 | Goldfarb et al. |
| 3,556,294 A | 1/1971 | Walck et al. |
| 3,567,820 A | 3/1971 | Sperti |
| 3,803,109 A | 4/1974 | Nemoto et al. |
| 3,967,728 A | 7/1976 | Gordon et al. |
| 4,308,120 A | 12/1981 | Pennewiss et al. |
| 4,323,547 A | 4/1982 | Knust et al. |
| 4,447,418 A | 5/1984 | Maddoux |
| 4,557,925 A | 12/1985 | Lindahl et al. |
| 4,664,114 A | 5/1987 | Ghodsian |
| 4,813,210 A | 3/1989 | Masuda et al. |
| 4,814,329 A | 3/1989 | Harsanyi et al. |
| 4,847,301 A | 7/1989 | Murray |
| 4,880,455 A | 11/1989 | Blank |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,937,254 A | 6/1990 | Sheffield et al. |
| 4,938,763 A | 7/1990 | Dunn et al. |
| 4,941,308 A | 7/1990 | Grabenkort et al. |
| 4,947,840 A | 8/1990 | Yannas et al. |
| 4,952,419 A | 8/1990 | de Leon |
| 4,968,302 A | 11/1990 | Schluter et al. |
| 5,017,229 A | 5/1991 | Burns et al. |
| 5,061,281 A | 10/1991 | Mares et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,176,956 A | 1/1993 | Jevne et al. |
| 5,179,174 A | 1/1993 | Elton |
| 5,202,310 A | 4/1993 | Levy et al. |
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,411,951 A | 5/1995 | Mitchell |
| 5,411,988 A | 5/1995 | Bockow et al. |

(Continued)

FOREIGN PATENT DOCUMENTS

| | | |
|---|---|---|
| EP | 0471566 | 2/1992 |
| EP | 0610731 | 8/1994 |

(Continued)

OTHER PUBLICATIONS

Notice of Allowance for U.S. Appl. No. 11/237,264 (listed on SB-08 as U.S. Publication No. US-2006-0067983), dated Mar. 27, 2014.
Notice of Allowance for U.S. Appl. 11/237,263 (listed on SB-08 as U.S. Publication No. US-2006-0110457), dated Mar. 27, 2014.
Ackman, R.G., "Fish Oils", *Bailey's Industrial Oil and Fat Products, 6th Edition*, 279-317 (2005).
Ahuja et al. Journal of Indian Pediatric Surgery 2002 7:15-20.

(Continued)

*Primary Examiner* — Robert A Wax
*Assistant Examiner* — Danah Al-Awadi
(74) *Attorney, Agent, or Firm* — Wesley Scott Ashton

(57) ABSTRACT

The present invention is generally directed to materials, gels, coatings and films prepared using a biomaterial (e.g., a fatty acid-based material comprising a network of cross-linked fatty acids) and a fixating material, layer or film (e.g., a fixating material comprising Na—CMC). The materials, gels, coatings and films disclosed herein can be used to facilitate the delivery of one or more therapeutic agents to a targeted tissue and a desired rate of release.

23 Claims, 8 Drawing Sheets

(56) References Cited

U.S. PATENT DOCUMENTS

| | | |
|---|---|---|
| 5,447,940 A | 9/1995 | Harvey et al. |
| 5,464,650 A | 11/1995 | Berg et al. |
| 5,480,653 A | 1/1996 | Aguadisch et al. |
| 5,509,899 A | 4/1996 | Fan et al. |
| 5,547,677 A | 8/1996 | Wright |
| 5,549,901 A | 8/1996 | Wright |
| 5,579,149 A | 11/1996 | Moret et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A | 1/1997 | Lichtenstein et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,629,021 A | 5/1997 | Wright |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,731,346 A | 3/1998 | Egberg et al. |
| 5,736,152 A | 4/1998 | Dunn |
| 5,747,533 A | 5/1998 | Egberg et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,048,725 A | 4/2000 | Shimada et al. |
| 6,056,970 A | 5/2000 | Greenawalt et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,366 B1 | 6/2001 | Popplewell et al. |
| 6,245,811 B1 | 6/2001 | Harrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,485,752 B1 | 11/2002 | Rein et al. |
| 6,491,938 B2 | 12/2002 | Kunz |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,696,583 B2 | 2/2004 | Koncar et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 | 8/2008 | Gottlieb et al. |
| 7,854,958 B2 * | 12/2010 | Kramer ..................... 427/2.1 |
| 7,947,015 B2 | 5/2011 | Herweck et al. |
| 8,124,127 B2 * | 2/2012 | Faucher et al. .......... 424/484 |
| 8,263,102 B2 | 9/2012 | Labrecque et al. |
| 8,308,684 B2 | 11/2012 | Herweck et al. |
| 8,312,836 B2 | 11/2012 | Corbeil et al. |
| 8,367,099 B2 | 2/2013 | Herweck et al. |
| 8,501,229 B2 | 8/2013 | Faucher |
| 8,722,077 B2 | 5/2014 | Labrecque et al. |
| 9,000,040 B2 | 4/2015 | Faucher et al. |
| 9,012,506 B2 | 4/2015 | Faucher et al. |
| 9,278,161 B2 | 3/2016 | Swanick et al. |
| 2001/0025034 A1 | 9/2001 | Arbiser |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |

(56) References Cited

U.S. PATENT DOCUMENTS

| | | |
|---|---|---|
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0009213 A1* | 1/2003 | Yang .................. A61F 2/07 623/1.13 |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 6/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0117007 A1 | 6/2004 | Whitbourne et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0137179 A1 | 7/2004 | Shojiro et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0124062 A1 | 6/2005 | Subirade |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0051544 A1 | 3/2006 | Goldmann |
| 2006/0058881 A1 | 3/2006 | Trieu |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1* | 6/2006 | Labrecque ............ A61L 31/148 424/423 |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0279929 A1 | 11/2008 | Devane et al. |
| 2008/0286440 A1 | 11/2008 | Scheer et al. |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0092665 A1 | 4/2009 | Mitra et al. |
| 2009/0181074 A1 | 7/2009 | Makower et al. |
| 2009/0181937 A1 | 7/2009 | Faucher et al. |
| 2009/0208552 A1 | 8/2009 | Faucher et al. |
| 2010/0183697 A1* | 7/2010 | Swanick et al. ............... 424/423 |
| 2010/0209473 A1 | 8/2010 | Dhont et al. |
| 2010/0233232 A1 | 9/2010 | Swanick et al. |
| 2011/0045050 A1 | 2/2011 | Elbayoumi et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |

(56) References Cited

FOREIGN PATENT DOCUMENTS

| | | |
|---|---|---|
| EP | 1520795 | 4/2005 |
| EP | 1557183 | 7/2005 |
| EP | 2083875 | 8/2009 |
| EP | 1402906 | 6/2011 |
| KR | 20080025986 | 3/2008 |
| WO | WO 1986/000912 | 7/1984 |
| WO | WO 1990/001969 | 3/1990 |
| WO | 90/008544 A1 | 8/1990 |
| WO | WO 1995/026715 | 10/1995 |
| WO | WO 1997/002042 | 1/1997 |
| WO | WO 1997/009367 | 3/1997 |
| WO | WO 1997/013528 | 4/1997 |
| WO | WO 1998/030206 | 7/1998 |
| WO | 98/46287 A2 | 10/1998 |
| WO | WO 1998/054275 | 12/1998 |
| WO | WO 1999/025336 | 5/1999 |
| WO | WO 2000/40278 | 7/2000 |
| WO | WO 2000/62830 | 10/2000 |
| WO | WO 2001/024866 | 4/2001 |
| WO | WO 2001/026585 | 4/2001 |
| WO | WO 2001/037808 | 5/2001 |
| WO | WO 2001/060586 | 8/2001 |
| WO | WO 2001/066036 | 9/2001 |
| WO | WO 2001/076649 | 10/2001 |
| WO | WO 2002/049535 | 6/2002 |
| WO | WO 2002/100455 | 12/2002 |
| WO | WO 2003/000308 | 1/2003 |
| WO | WO 2003/015748 | 2/2003 |
| WO | WO 2003/028622 | 4/2003 |
| WO | WO 2003/037397 | 5/2003 |
| WO | WO 2003/037398 | 5/2003 |
| WO | WO 2003/039612 | 5/2003 |
| WO | WO 2003/041756 | 5/2003 |
| WO | WO 2003/070125 | 8/2003 |
| WO | WO 2003/092741 | 11/2003 |
| WO | WO 2003/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | 20040101010 A1 | 11/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | 2008/010788 A2 | 1/2008 |
| WO | 2008/016664 A2 | 2/2008 |
| WO | WO 2008/057328 | 5/2008 |
| WO | 2010/042134 A1 | 4/2010 |
| WO | 2010/042241 A1 | 4/2010 |
| WO | WO 2012/009707 | 1/2012 |

OTHER PUBLICATIONS

Andes, et al. "Antiproliferative Strategies for the Treatment of Vascular Proliferative Disease", Current Vascular Pharmacology, 1)1): 85-98 (2003).

A paper entitled "Evaluation of the Biocompatibility and Drug Delivery Capabilities of Biological Oil Based Stent Coatings" by Shengqio Li of the Katholieke Universiteit Leuven.

Autosuture, "ParietexTM Composite OS Series Mesh," retrieved online at http://www.autosuture.com/AutoSuture/pagebuilder.aspx?topicID=135734&breadcrumbs=135601:0 (2007).

Binder et al., "Chromatographic Analysis of Seed Oils. Fatty Acid Composition of Castor Oil," The Journal of the American Oil Chemists' Society, vol. 39:513-517 (1962).

Camurus, "In our endeavors to create the unique, we start with the best. Your product."

CECW-EE, "Ch. 4: Coating Types and Characteristics," Engineering and Design—Painting: New Construction and Maintenance, pp. 4-1 to 4-24 (1995).

Crivello et al., "Epoxidized triglycerides as renewable monomers in photoinitiated cationic polymerization," Chem. Mater, 1992:692-699.

De Scheerder, Ivan K., et al. "Biocompatibility of polymer-coated oversized metallic stents implanted in normal porcine coronary arteries," Atherosclerosis, vol. 114:105-114.

Drummond, Calum J., et al., "Surfactant self-assembly objects as novel drug delivery vehicles," Current Opinion in Colliod & Interface Science, vol. 4:449-456 (2000).

Encylopedia Britannica Online, "Surface Coating," available online at http://www.britannica.com/Ebchecked/topic/575029/surface-coating>, date accessed Jun. 17, 2011.

Engstrom, Sven, "Drug Delivery from Cubic and Other Lipid-water Phases," Lipid Technology, vol. 2(2):42-45 (1990).

Guler, et al. "Some empirical equations for oxopolymerization of linseed oil," Progress in Organic Coatings, vol. 51:365-371 (2004).

Hwang, Chao-Wei, et al, "Physiological Transport Forces Govern Drug Distribution for Stent-Based Delivery," Circulation, vol. 104:600-605 (2001).

Jonasson, Lena et al., "Cyclosporon A inhibits smooth muscle proliferation in the vascular response to injury," Proc. Natl. Acad. Sci. USA, vol. 85: 2303-2306 (1988).

Jorge, N., "Grasas y Aceites", 48(1): 17-24, (1997).

Lipids, Chapter 19, pp. 1-12 (2002).

Mallegol, et al., "Drier Influence on the Curing of Linseed Oil," Progress in Organic Coatings 39:107-113 (2000).

Morse, Richard "Molecular Distillation of Polymerized Drying Oils," Industrial and Engineering Chemisry 33:1039-1043 (1941).

Oberhoff, Martin, et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).

Ogunniyi, D.S., "Castor oil: A vital industrial raw material," Biosource Technology, vol. 97: 1086-1091 (2006).

Polymerization Merriam-Webster Online Dictionary, retrieved from <www.merriam-webster.com> on Dec. 13, 2009; Merriam-Webster's Inc. 2009; pp. 1.

Redman, L.V. et al., "The drying rate of raw paint oils—a comparison," The Journal of Industrial and Engineering Chemistry, vol. 5: 630-636 (1913).

Rutkow, Ira M. et al., "'Tension-free' inguinal herniorrhaphy: A preliminary report on the 'mesh plug' technique," Surgery, vol. 114:3-8 (1993).

Salu, Koen J., et al, "Addition of cytochalasin D to a biocompatible oil stent coating inhibits intimal hyperplasia in a porcine coronary model," Coronary Artery Disease, vol. 14(8):545-555 (2003).

Scheller, Bruno, et al, "Addition of Paclitaxel to Contrast Media Prevents Restenosis After Coronary Stent Implantation," Journal of the American College of Cardiology, vol. 42(8):1415-1420 (2003).

Shahidi, Fereidoon ed.; "Bailey's Industrial Oil and Fats Products" 2005; John Wiley and Sons; vol. 5, Edible Oil and Fat Products: Processing Technologies, pp. 1-15.

Timar-Balizsy et al., "Chemical Principals of Textile Conservation," Oxford: Elsevier Science Ltd., 1998:117-119.

Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).

Websters Dictionary Online, Accessed on Feb. 13, 2009, entry for "polymer" p. 1 of 1.

Wikipedia, "Sirolimus," pp. 1-13, available online at http://en.wikipedia.org/wiki/Sirolimus, date accessed May 11, 2011.

Winter, et al., "Physical and Chemical Gelation" Encyclopedia of Materials—Science and Technology, vols. 1-11: 6691-6999 (2001).

International Search Report for International Application PCT/US05/034601, dated Apr. 10, 2006.

International Search Report for International Application PCT/US05/034610, dated Mar. 16, 2006.

(56) References Cited

OTHER PUBLICATIONS

International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
International Search Report for International Application No. PCT/US05/34941, dated May 4, 2006.
Supplementary European Search Report for Application No. EP 08877338.7, dated Aug. 16, 2012.
Supplementary European Search Report for Application No. EP09819594.4, dated Aug. 14, 2012.
International Search Report for PCT/US2011/44292, dated Dec. 6, 2011.
Supplementary European Search Report for Application No. EP 12004057, dated Apr. 10, 2013.
Non-final Office Action for U.S. Appl. No. 11/236,908 (listed on SB/08 as US 2006/0067974), dated Mar. 25, 2006.
Final Office Action for U.S. Appl. No. 11/236,908 (listed on SB/08 as US 2006/0067974), dated May 17, 2011.
Non-final Office Action for U.S. Appl. No. 11/236,908 (listed on SB/08 as US 2006/0067974), dated Aug. 24, 2009.
Non-final Office Action for U.S. Appl. No. 11/236,977 (listed on SB/08 as US 2006/0088596), dated Aug. 3, 2009.
Final Office Action for U.S. Appl. No. 11/237,263 (listed on SB/08 as US 2006/0110457), dated Jul. 7, 2010.
Non-final Office Action for U.S. Appl. No. 11/237,263 (listed on SB/08 as US 2006/0110457), dated Oct. 7, 2009.
Final Office Action for U.S. Appl. No. 11/237,264 (listed on SB/08 as US 2006/0067983), dated Jun. 2, 2010.
Non-final Office Action for U.S. Appl. No. 11/237,264 (listed on SB/08 as US 2006/0067983), dated Oct. 5, 2009.
Final Office Action for U.S. Appl. No. 11/701,799 (listed on SB/08 as US 2008/0109017), dated Nov. 23, 2010.
Non-final Office Action for U.S. Appl. No. 11/237,420 (listed on SB/08 as US 2006/0078586), dated Mar. 5, 2009.
Final Office Action for U.S. Appl. No. 11/237,420 (listed on SB/08 as US 2006/0078586), dated Nov. 4, 2009.
Non-final Office Action for U.S. Appl. No. 11/237,420 (listed on SB/08 as US 2006/0078586), dated Dec. 6, 2010.
Non-final Office Action for U.S. Appl. No. 11/238,532 (listed on SB/08 as US 2006/0067976), dated Mar. 30, 2009.
Final Office Action for U.S. Appl. No. 11/238,532 (listed on SB/08 as US 2006/0067976), dated Sep. 9, 2009.
Final Office Action for U.S. Appl. No. 11/238,554 (listed on SB/08 as US 2006/0121081), dated May 12, 2010.
Non-final Office Action for U.S. Appl. No. 11/238,554 (listed on SB/08 as US 2006/0121081), dated Oct. 9, 2009.
Final Office Action for U.S. Appl. No. 11/238,554 (listed on SB/08 as US 2006/0121081), dated May 1, 2009.
Non-final Office Action for U.S. Appl. No. 11/238,554 (listed on SB/08 as US 2006/0121081), dated Jul. 25, 2008.
Non-final Office Action for U.S. Appl. No. 11/238,564 (listed on SB/08 as US 2006/0083768), dated Apr. 16, 2008.
Final Office Action for U.S. Appl. No. 11/238,564 (listed on SB/08 as US 2006/0083768), dated Aug. 6, 2009.
Non-final Office Action for U.S. Appl. No. 11/239,555 (listed on SB/08 as US 2006/0067977), dated Mar. 30, 2009.
Non-final Office Action for U.S. Appl. No. 11/525,328 (listed on SB/08 as US 2007/0084144), dated Apr. 30, 2007.
Non-final Office Action for U.S. Appl. No. 11/525,390 (listed on SB/08 as US 2007/0071798), dated Jul. 14, 2010.
Final Office Action for U.S. Appl. No. 11/525,390 (listed on SB/08 as US 2007/0071798), dated Feb. 21, 2011.
Final Office Action for U.S. Appl. No. 11/582,135 (listed on SB/08 as US 2007/0202149), dated May 12, 2011.
Non-final Office Action for U.S. Appl. No. 11/582,135 (listed on SB/08 as US 2007/0202149), dated Nov. 9, 2010.
Non-final Office Action for U.S. Appl. No. 11/582,135 (listed on SB/08 as US 2007/0202149), dated Jan. 6, 2010.
Non-final Office Action for U.S. Appl. No. 11/582,135 (listed on SB/08 as US 2007/0202149), dated May 12, 2009.
Non-final Office Action for U.S. Appl. No. 11/701,799 (listed on SB/08 as US 2008/0109017), dated Apr. 12, 2010.
Non-final Office Action for U.S. Appl. No. 11/978,840 (listed on SB/08 as US 2008/0118550), dated Dec. 3, 2010.
Non-final Office Action for U.S. Appl. No. 11/980,155 (listed on SB/08 as US 2008/0113001), dated Mar. 24, 2011.
Non-final Office Action for U.S. Appl. No. 12/075,223 (listed on SB/08 as US 2008/0206305), dated Dec. 8, 2010.
Non-final Office Action for U.S. Appl. No. 12/325,546 (listed on SB/08 as US 2009/0181937), dated Feb. 25, 2010.
Final Office Action for U.S. Appl. No. 12/325,546 (listed on SB/08 as US 2009/0181937), dated Aug. 31, 2010.
Non-final Office Action for U.S. Appl. No. 12/364,763 (listed on SB/08 as US 2009/0208552), dated Dec. 11, 2009.
Final Office Action for U.S. Appl. No. 12/364,763 (listed on SB/08 as US 2009/0208552), dated Sep. 21, 2010.
Interview summary for U.S. Appl. No. 11/236,908 (listed on SB/08 as US 2006/0067974) dated May 5, 2009.
Interview summary for U.S. Appl. No. 11/236,908 (listed on SB/08 as US 2006/0067974) dated Dec. 2, 2010.
Interview summary for U.S. Appl. No. 11/237,420 (listed on SB/08 as US 2006/0078586) dated May 5, 2009.
Interview summary for U.S. Appl. No. 11/582,135 (listed on SB/08 as US 2007/0202149) dated Dec. 7, 2010.

(56) References Cited

OTHER PUBLICATIONS

Interview summary for U.S. Appl. No. 12/325,546 (listed on SB/08 as US 2009/0181937) dated Dec. 2, 2010.
Interview summary for U.S. Appl. No. 12/364,763 (listed on SB/08 as US 2009/0208552) dated Dec. 2, 2010.
Final Office Action for U.S. Appl. No. 11/237,420 (listed on SB/08 as US 2006/0078586), dated Jul. 13, 2011.
Final Office Action for U.S. Appl. No. 11/978,840 (listed on SB/08 as US 2008/0118550), dated Jun. 22, 2011.
Final Office Action for U.S. Appl. No. 12/075,223 (listed on SB/08 as US 2008/0206305), dated Aug. 11, 2011.
Non-final Office Action for U.S. Appl. No. 11/525,390 (listed on SB/08 as US 2007/0071798), dated Jul. 11, 2011.
Non-Final Office Action for U.S. Appl. No. 11/701,799 (listed on SB/08 as US 2008/0109017), dated Aug. 17, 2011.
Non-Final Office Action for U.S. Appl. No. 11/582,135 (listed on SB/08 as US-2007-0202149), dated Oct. 14, 2011.
Final Office Action for U.S. Appl. No. 11/980,155 (listed on SB/08 as US-2008-0113001), dated Oct. 21, 2011.
Non-Final Office Action for U.S. Appl. No. 11/236,908 (listed on SB/08 as US-2006-0067974), dated Dec. 2, 2011.
Non-Final Office Action for U.S. Appl. No. 12/182,261 (listed on SB/08 as US 2009-0047414), dated Dec. 21, 2011.
Non-Final Office Action for U.S. Appl. No. 12/401,243 (listed on SB/08 as US 2010-0233232), dated Jan. 5, 2012.
Notice of Allowance for U.S. Appl. No. 11/582,135 (listed on SB/08 as US 2007-0202149), dated Jan. 9, 2012.
Non-Final Office Action for U.S. Appl. No. 12/182,165 (listed on SB/08 as US 2009-0011116), dated Jan. 5, 2012.
Final Office Action for U.S. Appl. No. 11/701,799 (listed on SB/08 as US 2008/0109017), dated Feb. 13, 2012.
Non-Final Office Action for U.S. Appl. No. 12/581,582 (listed on SB/08 as US 2010-0183697), dated Mar. 14, 2012.
Final Office Action for U.S. Appl. No. 12/182,165 (listed on SB/08 as US 2009-0011116), dated Apr. 6, 2012.
Final Office Action for U.S. Appl. No. 12/182,261 (listed on SB-08 as US 2009/0047414) dated Apr. 30, 2012.
Notice of Allowance for U.S. Appl. No. 11/236,908 (listed on SB/08 as US-2006-0067974), dated May 11, 2012.
Final Office Action for U.S. Appl. No. 12/401,243 (listed on SB/08 as US-2010-0233232), dated Jun. 11, 2012.
Notice of Allowance for U.S. Appl. No. 12/182,261 (listed on SB/08 as US US-2009-0047414), dated Jul. 23, 2012.
Advisory Action for U.S. Appl. No. 12/401,243 (listed on SB/08 as US 2010-0233232), dated Aug. 27, 2012.
Final Office Action for U.S. Appl. No. 12/581,582 (listed on SB-08 as US 2010/0183697) dated Aug. 29, 2012.
Notice of Allowance for U.S. Appl. No. 11/525,390 (listed on SB/08 as US-2007/0071798), dated Oct. 4, 2012.
Final Office Action for U.S. Appl. No. 11/236,943 (listed on SB/08 as US 2006/0067975), dated Dec. 23, 2009.
Non-Final Office Action for U.S. Appl. No. 11/236,943 (listed on SB/08 as US 2006/0067975), dated Mar. 5, 2009.
Advisory Action for U.S. Appl. No. 12/581,582 (listed on SB/08 as US 2010-0183697), dated Nov. 14, 2012.
Non-Final Office Action for U.S. Appl. No. 13/404,487 (listed on SB/08 as 2012-0213839), dated Dec. 20, 2012.
Notice of Allowance for U.S. Appl. No. 11/525,390 (listed on SB/08 as US-2007/0071798), dated Nov. 20, 2012.
Notice of Allowance for U.S. Appl. No. 11/525,390 (listed on SB/08 as US-2007/0071798), dated Nov. 30, 2012.
Advisory Action for U.S. Appl. No. 12/581,582 (listed on SB-08 as U.S. Publication No. 2010-0183697), dated Nov. 14, 2012.
Notice of Allowance for U.S. Appl. No. 11/525,390 (listed on SB-08 as U.S. Publication No. US-2007-0071798), dated Nov. 20, 2012.
Non-Final Office Action for U.S. Appl. No. 13/404,487 (listed on SB-08 as US 2012-0213839), dated Dec. 20, 2012.
Non-Final Office Action for U.S. Appl. No. 13/184,512 (listed on SB-08 as 2012-0016038), dated Jan. 31, 2013.
Non-Final Office Action for U.S. Appl. No. 11/978,840 (listed on SB-08 as U.S. No. US-2008-0118550), dated Feb. 19, 2013.
Non-Final Office Action for U.S. Appl. No. 13/682,991 (listed on SB-08 as U.S. No. US-2013-0074452), dated Mar. 18, 2013.
Notice of Allowance for U.S. Appl. No. 13/404,487 (listed on SB-08 as U.S. No. US-2012-0213839), dated Apr. 2, 2013.
Non-Final Office Action for U.S. Appl. No. 11/236,943 (listed on SB-08 as U.S. No. US-2006-0067975), dated Apr. 22, 2013.
Final Office Action for U.S. Appl. No. 13/184,512 (listed on SB-08 as U.S. No. U.S. 2012-0016038), dated Jun. 25, 2013.
Non-Final Office Action for U.S. Appl. No. 11/237,264 (listed on SB-08 as U.S. No. US-2006-0067983), dated Jul. 3, 2013.
Non-Final Office Action for U.S. Appl. No. 13/593,656 (listed on SB-08 as U.S. No. US-2012-03115219), dated Jul. 15, 2013.
Mallegol, "Long-Term Behavior of Oil-Based Varnishes and Paints Photo-and Thermooxidation of Cured Linseed Oil", *Journal of the American Oil Chemists' Society*, 77:257-263 (2000).
International Search Report for International Application PCT/US2013/044653, dated Sep. 4, 2013.
Non-Final Office Action for U.S. Appl. No. 11/237,420 (listed on SB-08 as U.S. Publication No. US-2006-0078586), dated Nov. 12, 2013.
Non-Final Office Action for U.S. Appl. No. 12/075,223 (listed on SB-08 as U.S. Publication No. US-2008-0206305), dated Nov. 12, 2013.
Non-Final Office Action for U.S. Appl. No. 11/980,155 (listed on SB-08 as U.S. Publication No. US-2008-0113001), dated Nov. 12, 2013.
Notice of Allowance for U.S. Appl. No. 13/682,991 (listed on SB-08 as U.S. Publication No. US 2013-0074452), dated Aug. 1, 2013.
Notice of Allowance for U.S. Appl. No. 11/978,840 (listed on SB-08 as U.S. Publication No. US-2008-0118550), dated Aug. 6, 2013.
Final Office Action for U.S. Appl. No. 11/236,943 (listed on SB-08 as U.S. Publication No. US-2006-0067975), dated Dec. 4, 2013.
Final Office Action for U.S. Appl. No. 11/237,264 (listed on SB-08 as U.S. Publication No. US-2006-0067983), dated Dec. 17, 2013.
Notice of Allowance for U.S. Appl. No. 13/593,656 (listed on SB-08 as U.S. Publication 2012-03115219), dated Jan. 24, 2014.
Final Office Action for U.S. Appl. No. 12/581,582, dated Jan. 8, 2015.
Non-Final Office Action for U.S. Appl. No. 12/401,243, dated Jan. 16, 2015.
Non-Final Office Action for U.S. Appl. No. 11/237,420, dated Jan. 21, 2015.
Notice of Allowance for U.S. Appl. No. 13/943,489, dated Jan. 29, 2015.
Non-Final Office Action for U.S. Appl. No. 11/980,155, dated Nov. 7, 2014.
Notice of Allowance for U.S. Appl. No. 12/364,763 (listed on SB-08 as U.S. Publication No. US-2009-0208552), dated Dec. 5, 2014.
Notice of Allowance for U.S. Appl. No. 12/325,546 (listed on SB-08 as U.S. Publication No. US-2009-0181937), dated Dec. 8, 2014.
Uchida, et al., "Swelling Process and Order-Disorder Transition of Hydrogel Containing Hydrophobic Ionizable Groups", *Macromolecules*, 28, 4583-4586 (1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum*, 47; 2157-2161 (2005).
Sano, et al., "A controlled Trial of Selegiline, Alpha-Tocopherol, or Both as Treatment for Alzheimer's Disease", *The New England Journal of Medicine*, 336; 1216-1222 (1997).
Supplementary European Search Report for Application No. EP 10825447, dated Mar. 31, 2014.
Non Final Office Action for U.S. Appl. No. 12/581,582 (listed on SB-08 as U.S. Publication 2010-0183697), dated May 29, 2014.
Non-Final Office Action for U.S. Appl. No. 13/943,489, dated Jul. 1, 2014.
Final Office Action for U.S. Appl. No. 11/980,155, dated Jul. 21, 2014.

(56) References Cited

OTHER PUBLICATIONS

Final Office Action for U.S. Appl. No. 11/237,420, dated Jul. 22, 2014.
Final Office Action for U.S. Appl. No. 12/075,223, dated Jul. 22, 2014.
Non Final Office Action for U.S. Appl. No. 12/325,546 (listed on SB-08 as U.S. Publication No. US-2009-0181937), dated Apr. 22, 2014.
Non Final Office Action for U.S. Appl. No. 12/364,763 (listed on SB-08 as U.S. Publication No. US-2009-0208552), dated Apr. 23, 2014.
Non Final Office Action for U.S. Appl. No. 12/401,243 (listed on SB/08 as US 2010-0233232), dated May 8, 2014.
Non-Final Office Action for U.S. Appl. No. 11/701,799, dated Jul. 22, 2014.
Notice of Allowance for U.S. Appl. No. 11/236,943 (listed on SB-08 as U.S. Publication No. US-2006-0067975), dated Oct. 6, 2014.
Non-Final Office Action for U.S. Appl. No. 13/184,512, dated Oct. 10, 2014.
Non-Final Office Action for U.S. Appl. No. 12/075,223, dated Oct. 29, 2014.
Final Office Action for U.S. Appl. No. 11/701,799, dated Mar. 12, 2015.
Final Office Action for U.S. Appl. No. 13/184,512, dated Apr. 28, 2015.
H. Fineberg et al., Industrial Use of Fish Oils, pp. 222-238, http://spo.nmfs.noaa.gov/Circulars/CIRC278.pdf, downloaded Aug. 3, 2015.
Lewis, Richard J., Sr., Hawley's Condensed Chemical Dictionary, 2001, pp. 308, 309 and 896-898, 14th edision, John Wiley & Sons, Inc., New York.
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
Triglycerides, https://www.lipid.org/sites/default/files/triglycerides.pdf (downloaded Sep. 24, 2015).
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).
Swanson, Danielle, et al., Omega-3 Fatty Acids EPA and DHA: Health Benefits Throughout Life, 3 Advances in Nutrition 1-7 (American Society for Nutrition 2012).
Fats & Oils (2008) at http://scifun.chem.wisc.edu/chemweek/pdf/fats&oils.pdf (downloaded Sep. 24, 2015).
Bacteria in Water, The USGS Water Science School, http://water.usgs.gov/edu/bacteria.html (downloaded Nov. 9, 2015).
Novotny, L. et al., Fish: a potential source of bacterial pathogens for human beings, VET. MED.—CZECH, 49, 2004, vol. 9, pp. 343-358.
Allergies, Asthma and Allergy Foundation of America (2011), http://www.aafa.org/page/types-of-allergies,aspx (downloaded Oct. 5, 2015).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (! 987).
Singh, Alok, et al., "Facilitated Stent Delivery Using Applied Topical Lubrication", Catherization and Cardiovascular Interventions, vol. 69, pp. 218-222 (2007).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Soy Allergy, Asthma and Allergy Foundation of America (2005), http://www.aafa.org/display.cfm?id=9&sub=20&cont=522 (downloaded Nov. 10, 2015).
Refined soybean oil not an allergen, say food scientists, FOOD navigator-usa.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).
Soy allergy, at http://www.mayoclinic.org/diseases-conditions/soy-allergy/basics/definition/con-20031370?p=1 (downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Hutlin, Herbert O. et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).
Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:lessionid=33N2RBQDV0DZKCQPCCEGU3AKB2IlWTT1 (2006).

(56) References Cited

OTHER PUBLICATIONS

Orthovisc, "What is Orthovisc®?" retrieved online at http://www.orthovisc.com/xhtmlbgdisplay.html?itemname=about_orthovisc (2005).

Orthovisc, "Your Knees and Osteoarthritis", retrieved online at http://www.orthovisc.com/xhtmlbgdisplay.jhtml?itemname=understanding_knee_oa (2003).

Orthovisc, "What to expect from your treatment," retrieved online at http://www.orthovisc.com/xhtmlbgdisplay.jhtml?itemname=what_to_expect (2007).

Orthovisc, "Tools and Resources for Managing Your Osteoarthritis", retrieved online at http://www.orthovisc.com/xhtmlbgdisplay.jhtml?itemname=patient_resources (2007).

Pohibinska, A., et al., "Time to reconsider saline as the ideal rinsing solution during abdominal surgery", The American Journal of Surgery, vol. 192, pp. 281-222 (2007).

Hortolam, Juliane G., et al., "Connective tissue diseases following silicone breast implantation: where do we stand?", Clinics, 2013, vol. 3, p. 281.

Lidar, M. et al., "Silicone and sclerodema revisited", Lupus, 2012, vol. 21, pp. 121-127.

"Lead", Article by Centers for Disease Control and Prevention (CDC), Nov. 2009, 2 pages.

"Cure" in Academic Press Dictionary of Science and Technology, 1992.

Wikipedia, Sunflower oil, https://en.wikipedia.org/wiki/Sunflower_oil, accessed Jul. 23, 2015 in related U.S. Appl. No. 14/252,671, pp. 1-7.

Esoteric Oils, Peppermint essential oil information, http://www.essentialoils.co.za/essential-oils/peppermint.htm, accessed Jul. 23, 2015 in related U.S. Appl. No. 14/252,671, pp. 1-7.

Orthomolecular, Fish Oil, Jun. 29, 2004, http://orthomolecular.org/nutrients/fishoil.html, accessed Jul. 22, 2015 in related U.S. Appl. No. 14/252,671, p. 1.

Wicks et al. Organic Coatings:Science and Technology 1999 New York:Wiley Interscience, pp. 258-267.

Mills et al. Oils and Fats. "The Organic Chemistry of Museum Objects" London:Buttersworth and Co. 1987, pp. 26-40.

Erhardt Paints Based on Drying Oil Media. Painted Wood: History & Conservation. Ed. Berland Singapore: The J. Paul Getty Trust 1998. pp. 17-32.

Wexler et al. Chemical Reviews 1964, vol. 64, No. 6, pp. 591-611.

Polymer—The Chambers 21st Century Dictionary M. Robinson and G. Davidson (Eds.), London, United Kingdom: Chambers Harrap. Retrieved from http://search.credoreference.com/content/entry/chambdict!polymer/O.

Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst!polymer/O.

Falagas et al. European Society of Clinical Microbiology and Infection Diseases, 2005, vol. 11, pp. 3-8.

Bimbo, INFORM 1998, vol. 9, No. 5, pp. 473-483.

Extended European Search Report dated Dec. 10, 2015 issued for corresponding EP Patent Application No. 13804477, 8 pages.

SepraFilm Adhesion Barrier package insert (Genzyme Biosurgery 2008).

Alessandro Sannino et al., Biodegradable Cellulose-based Hydrogels: Design and Applications, 2 Materials 353-373 (2009).

Thomas Heinz, Carboxymethyl Ethers of Cellulose and Starch—A Review, Center of Excellence for Polysaccharide Reseach, Friedrich Schiller University of Jena (Germany), pp. 13-29 (2005).

H. Omidian et al., Swelling Agents and Devices in Oral Drug Delivery, J. Drug. Del. Sci. Tech., 18 (2) 83-93 (2008).

S. Kamel et al., Pharmaceutical Significance of Cellulose: A Review, eXPRESS Polymer Letters vol. 2, No. 11 pp. 758-778 (2008).

A. M. Adel et al. Carboxymethylated Cellulose Hydrogel; Sorption Behavior and Characterization, Nature and Science, 8(8), pp. 244-256, (2010).

Final Office Action dated Mar. 30, 2017 for related U.S. Appl. No. 11/237,420, 20 pages.

Henderson, R. James et al., "Hydrolysis of Fish Oils Containing Polymers of Triacylglycerols by Pancreatic Lipase in vitro", LIPIDS, vol. 28, No. 4, 1993, pp. 313-319.

\* cited by examiner

Depiction of the molecular structure of sodium carboxymethylcellulose polymer
*The substituted functional group of interest (carboxylate ion) is indicated.*

Film Images and Drug Release Profiles
(a) Drug applied to CMC side, Image: Film lot #LC112-099C, Curve: MIT01-163B;
(b) Drug applied to omega-3 fatty acid side, Film Lot LC112-099D, Curve: MIT01-163A; and
(c) NBD-Stearate Fatty Acid Dissolution from film lot 00620-49 in Simulated Peritoneal Fluid Film Mass Changes as Function of Time in Simulated Peritoneal Fluid (0.5 mil and 4.0 mil films)
The release curves have been fit to a bi-phasic model. The respective exponential decay equations are:
0.5 mil: $M = 32.6e^{-0.0079t} + 79.67e^{-0.0806t}$, $r^2 = 0.9988$
4.0 mil: $M = 57.1e^{-0.0031t} + 57.8e^{-0.1448t}$, $r^2 = 0.9986$.

Effects of Packaging Humidity on CMC-Cured Oil FTIR Protonation Peak Ratio (1720 cm$^{-1}$/1024 cm$^{-1}$).

US 9,867,880 B2

CURED OIL-HYDROGEL BIOMATERIAL COMPOSITIONS FOR CONTROLLED DRUG DELIVERY

RELATED APPLICATION

This application claims priority to, and the benefit of, U.S. Provisional Application No. 61/659,301, filed Jun. 13, 2012. The entire teachings of the above application are incorporated herein by reference.

FIELD OF THE INVENTION

The present inventions relate to coatings and materials that generally comprise a biomaterial layer and a fixating or adhesive layer and to related methods of using such layers to influence the physical properties and behavior of the resulting coatings and materials, including with respect to drug delivery.

BACKGROUND OF THE INVENTION

U.S. Publication No. 2012/0016038, presented the ability to alter the hydrolysis rate of biocompatible cured oil compositions by altering the underlying fatty acid content of the starting material. The application also demonstrated that the rate of hydrolysis of the oil composition could be directly altered as a means to control the delivery rate of therapeutics. U.S. Publication No.: 2010/0183697 discloses the ability to couple non-cross-linked CMC and chitosan hydrogels to cured oil materials for use as an adhesion barrier was presented.

Needed are novel materials and related methods of manipulating the properties of films, anti-adhesion layers, coatings, gels and adhesive layers. Also needed are novel methods of preparing coating materials that have desired properties and that can be manipulated to achieve one or more desired outcomes or characteristics, such as the rate of hydrolysis or adhesive properties.

SUMMARY OF THE INVENTION

The present invention is generally directed to materials prepared using a network of cross-linked fatty acids (e.g., omega-3 fatty acids) that can be implanted as a film, anti-adhesion layer, coating material or gel, and in certain embodiments can be used for or to facilitate delivery of one or more therapeutic agents. The present invention is also directed to such anti-adhesion materials, layers, films, coatings and gels that can be prepared with an outer adhesive layer, such as a fixating or mucoadhesive layer (e.g., a layer comprising carboxymethylcellulose or CMC). By thermally-inducing cross-linking of fatty acids (e.g., omega-3 fatty acids) the properties of the resulting materials (e.g., polarity, rate of hydrolysis and/or bioabsorbability) can be tuned or otherwise manipulated by modulating the fatty acid composition of the material. In certain embodiments, the materials disclosed herein (e.g., films, coatings, gels and barrier layers) can be used to facilitate the delivery of therapeutic agents to a target tissue at a defined rate, as release from such materials predominantly results from material bio-erosion rather than out-diffusion. For example, hydrolysis and enzymatic hydrolysis or degradation (and therefore in vivo bioabsorption) of such materials may be controlled by the initial fatty acid composition and regulated hydrolysis creates biocompatible (e.g., non-inflammatory) break-down products of fatty acids, glycerols and glycerides.

Also disclosed herein is that in certain embodiments the addition or inclusion of an additional fixating or mucoadhesive layer (e.g., carboxymethylcellulose or CMC) imparts in situ adhesive capacity ensuring construct retention at the application site, and can further influence drug delivery rates. In certain embodiments, one or more of the layers (e.g., the biomaterial layer and/or the fixating layer) comprise one or more therapeutic agents and are capable of delivering such therapeutic agents to a targeted tissue at a defined rate of release. In some embodiments, the one or more therapeutic agents may be hydrophobic. In yet other embodiments, the one or more therapeutic agents may be hydrophilic. In certain embodiments, the one or more therapeutic agents may comprise paclitaxel.

Described herein are relationships between the properties of such layers and methods of tailoring the release of therapeutic agents from such layers by manipulating the properties of the materials. For example, in certain embodiments described herein, the rate at which one or more therapeutic agents is released from the biomaterial and/or fixating layers can be manipulated (e.g., increased or decreased). For example, in certain embodiments the dissolution of the biomaterial layer (e.g., a film comprising fatty acids, such as omega-3 fatty acids) follows a bi-phasic release that can be described mathematically as the sum of two exponential decay equations. The first phase is a rapid burst and is followed by a slower decay of material. These various phases of the release may be tailored to deliver active pharmaceutical ingredients (API's) or one or more therapeutic agents.

Also disclosed herein are means of manipulating, modulating, or otherwise controlling the rate of release of one or more therapeutic agents from the materials disclosed herein by coupling one or more fixating layers (e.g., a carboxymethylcellulose hydrogel formulations) to the biomaterial (e.g., a film comprising cross-linked fatty acids) with the composition of the biomaterial providing an additional means of controlling drug delivery via the fixating layer in addition to the biomaterial layer. For example, such a material prepared by coupling a biomaterial layer to a fixating layer (i.e., a hybrid hydrogel-oil composition) can be tailored to deliver either a single or multiple therapeutic agents with different elution rates, depending on the origin of release from the fatty acid-based material or matrix.

In accordance with the present invention, disclosed herein are coating materials (e.g., bioabsorbable coating materials) for medical devices comprising a biomaterial, a fixating material (e.g., sodium carboxymethylcellulose) and at least one therapeutic agent; wherein the biomaterial includes fatty acids (e.g., fish oil fatty acids) cross-linked to each other (e.g., directly to each other); wherein the fixating material is disposed on an outer surface of the biomaterial relative to the medical device; wherein the coating material effects controlled delivery in a patient of the one or more therapeutic agent from the coating material; and wherein the controlled delivery is at least partially characterized by the total and relative amounts of the biomaterial and the fixating material in the film material. In certain embodiments, the rate of release of the one or more therapeutic agents from the fixating material may be controlled at least in part by the degree of protonation of the fixating material caused by the relative amount of fatty acids in the biomaterial.

Also disclosed herein are methods of modulating the rate of release of one or more therapeutic agents from a coating material. Such methods include the steps of providing a biomaterial, wherein the biomaterial comprises fatty acids cross-linked to each other; providing a fixating material; and coupling the fixating material to the biomaterial to form the coating material; wherein at least one of the biomaterial and the fixating material comprises one or more therapeutic agents; and wherein the rate of release the one or more therapeutic agents from the coating material is at least partially characterized by total and relative amounts of the biomaterial and the fixating material in the coating material.

In accordance with the present invention, films can include a biomaterial, wherein the biomaterial comprises fatty acids cross-linked to each other; and a fixating material, wherein the fixating material is disposed on an outer surface of the biomaterial relative to the medical device; wherein at least one of the biomaterial and the fixating material comprises one or more therapeutic agents; wherein the film is implantable in a patient to effect controlled delivery of the one or more therapeutic agent to the patient; and wherein the controlled delivery is at least partially characterized by total and relative amounts of the biomaterial and the fixating material in the film. In accordance with aspects of the present invention, the rate of release of the one or more therapeutic agents from the fixating material is controlled at least in part by the degree of protonation of the fixating material caused by the relative amount of fatty acids in the biomaterial.

In accordance with the present invention, the biomaterials disclosed herein can include a first therapeutic agent and the fixating material comprises a second therapeutic agent; wherein the biomaterial releases the first therapeutic agent at a first rate and the fixating material releases the second therapeutic agent at a second rate. The second rate may be influenced by a composition of the biomaterial. For example, in certain embodiments wherein the biomaterial has a high fatty acid density, such high fatty acid density delays the second rate. In other embodiments wherein the biomaterial has a low fatty acid density, such low fatty acid density accelerates the second rate.

In accordance with the present invention, the rate of release of the one or more therapeutic agents from the fixating material is controlled at least in part by the degree of protonation of the fixating material caused by a relative amount of fatty acids in the biomaterial. For example, the rate of release of the one or more therapeutic agents from the fixating material may be controlled at least in part by the degree of protonation of the fixating material caused by a relative amount of fatty acids in the biomaterial. In certain embodiments, a greater total and relative amount of the biomaterial to the fixating material in the coating results in a higher degree of protonation of the fixating material and thereby extends the release of the one or more therapeutic agents from the fixating material.

In accordance with the present invention, the biomaterials disclosed herein further comprise alpha-tocopherol. Similarly, in certain embodiments, the biomaterial further comprises a naturally-occurring oil (e.g., fish oil). In accordance with the present invention, the fatty acids are fish oil fatty acids (e.g., omega-3 fatty acids). For example, the biomaterial may comprise one or more omega-3 fatty acids selected from the group consisting of eicosapentaenoic acid (EPA) and docosahexaenoic acid (DHA), and combinations thereof. In accordance with the present invention, the biomaterial further comprises ethyl esters of one or more fatty acids (e.g., ethyl esters of omega-3 fatty acids such as eicosapentaenoic acid (EPA), docosahexaenoic acid (DHA) and combinations thereof).

Also disclosed herein are fixating materials that are capable of fixating the coatings to tissue in vivo for a duration of greater than 10 days. In those embodiments where the fixating material includes one or more therapeutic agents, such one or more therapeutic agents may be released from the fixating material for a duration of greater than 10 days (e.g., at least about 10 days, 14 days, 21 days, 24 day, 30 days, 45 days, 60 days, 90 days or more). In accordance with the present invention, the fixating materials may be selected from the group consisting of carboxymethylcellulose (Na—CMC), poly(ethylene glycol), poly(ethylene oxide), poly(HEMA), poly(N-vinyl pyrrolidone), poly (acrylic acid), carboxymethyl cellulose (CMC), chitosan and combinations thereof.

The coating materials disclosed herein may be applied to a medical device (e.g., a medical device selected from the group consisting of a surgical mesh, a graft, a catheter balloon, a stand-alone film and a stent) and cured (e.g., heat cured) on the medical device.

In accordance with the present invention, the coating materials disclosed herein may further comprise a plasticizing agent. For example, such coating materials may comprise a plasticizing agent selected from the group consisting of glycerin, propylene glycol, poly ethylene glycol, triacetin citrate, triacetin and combinations thereof.

The above discussed and many other features and attendant advantages of the present invention will become better understood by reference to the following detailed description of the invention when taken in conjunction with the accompanying examples.

BRIEF DESCRIPTION OF THE DRAWINGS

The aforementioned features and advantages, and other features and aspects of the present invention, will become better understood with regard to the following description and accompanying drawings, wherein:

FIG. 2A depicts the percentage of therapeutic agent released from the fixating material (CMC) side of the film. FIG. 2B depicts the percentage of therapeutic agent released from the biomaterial (omega-3 fatty acid) side of the film. FIG. 2C depicts the erosion of the fatty acid-based biomaterial in simulated peritoneal fluid as a function of time;

DETAILED DESCRIPTION OF THE INVENTION

Figure 1:
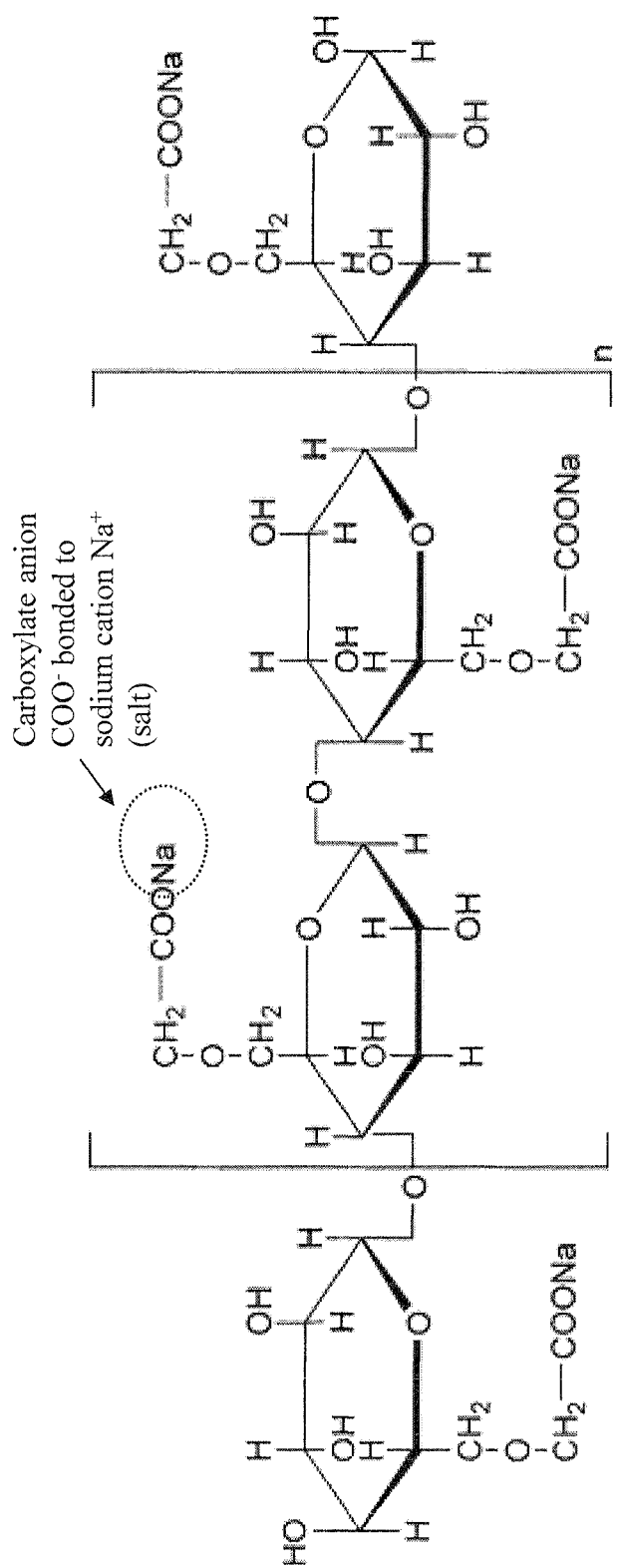
FIG. 1 depicts the molecular structure of sodium carboxymethylcellulose (CMC) and in particular illustrates the ionic interaction of the CMC carboxylate anion and the sodium cation.

The ionically charged state of a fixating or hydrogel material (e.g., a film comprising CMC) is critical for tissue attachment, as well as the aqueous solubility of the fixating or hydrogel material and, in accordance with the present invention, may be manipulated to modulate (e.g., increase or decrease) the ability of such material not only to adhere to tissue but also to deliver therapeutic agents. There are chemical interactions between the fixating hydrogel material or layer and the biomaterial layer (e.g., a cured oil composition) where the amount of, and underlying fatty acid chemistry of, the biomaterial layer (e.g., a cured oil composition) can be utilized to modify the charged state of the fixating or hydrogel layer. This technique can therefore be used to alter the hybrid hydrogel-oil material's affinity for tissue adhesion, the material's water solubility characteristics, and the material's propensity for controlled drug and/or therapeutic delivery to surrounding tissue at desired or predetermined rates.

As described in U.S. Publication No. 2012/0016038, the entire teachings of which are incorporated by reference herein, the underlying fatty acid chemistry of the fatty acid-based material allows for a means to manipulate the hydrolysis of such material. The present inventors have discovered that the material's in-vitro hydrolysis correlate with in-vivo absorption properties of such material and may be used to define the mechanism of release (e.g., monophasic or biphasic release). The term "monophasic" refers to the classic exponential decay model. This implies that only one mechanism of omega-3 fatty acid hydrolysis is occurring. This model is consistent with a completely cross-linked polymer whose hydrolysis occurs by only one pathway. The following equation is used to fit the data:

$$M = M_0 e^{-kt}$$

where, "M" refers to the amount of material that is remaining, $M_0$ is the starting amount of material, and "k" is the rate constant.

As used herein, the term "bi-phasic" means that the release is being fit to an exponential decay model that describes two decay phenomena that simultaneously occur. For the fatty acid-based coating materials disclosed herein (e.g., omega-3 fatty acid based coating materials), this may be the release of "unbound" or unreacted fatty acids by means of swelling and diffusion as well as the release of "bound" or reacted fatty acids by hydrolytic reactions. Alternatively, bi-phasic behavior may be described by the combination of other decay phenomena such as the relative rates of hydrolysis of different bonds, or the relative rates of hydrolytic and enzymatic actions. In the case of omega-3 fatty acid coating materials, the data is fit to the following model that is the sum of the two decays:

$$M = M_1 e^{-k_1 t} + M_2 e^{-k_2 t}$$

where "M" refers to the amount of material that is remaining, $M_1$ is the starting amount of unreacted material, $M_2$ is the starting amount of reacted material, and $k_1$ and $k_2$ are their respective rate constants.

As used herein, to describe a material, layer or gel the phrase "biomaterial" refers to a material that comprises fatty acids (e.g., omega-3 fatty acids). In certain embodiments, such biomaterial can effectively reduce the incidence of adhesions (e.g., post-operative adhesions). In certain embodiments, such biomaterial layer or material is prepared by exposing an oil composition (e.g., a naturally- or synthetically-prepared oil) to curing conditions (e.g., thermal or UV curing conditions) to induce cross-linking (e.g., oxidative cross-linking) of the fatty acids that comprise such oil composition (e.g., cross-linking of fatty acids directly to each other by way of one or more carbon-carbon, ether, ester, lactone and delta-lactone bonds). In certain embodiments, such biomaterial layers are non-polymeric. In certain embodiments, the biomaterial layer may be used as a carrier to facilitate the delivery of one or more therapeutic agents. In certain embodiments, a fixating layer or material is disposed onto the biomaterial layer.

In certain embodiments, the materials, films and related methods disclosed herein contemplate the use of a fixating material or layer. Such fixating material facilitates the adhesion of the material and films to tissue in vivo. As used herein, the phrases "fixating material" and "fixating layer" are used to describe a material having mucoadhesive properties. In certain embodiments, the mucoadhesive properties are imparted to the material or layer by the inclusion of one or more polymers (e.g., Na—CMC). In certain embodiments, the fixating material comprises one of a group of sodium carboxymethylcellulose (Na—CMC), poly(ethylene glycol), poly(ethylene oxide), poly(HEMA), poly(N-vinyl pyrrolidone), poly(acrylic acid), carboxymethyl cellulose (CMC), and chitosan. In certain embodiments, the fixating material is sodium carboxymethylcellulose (Na—CMC).

An important attribute of the mucoadhesive properties of the CMC component in cured oil-CMC hybrid materials is the maintaining of the sodium salt form (FIG. 1) so that the negative charge produced after displacement of the sodium upon hydration can couple to the positive charge produced by amino groups of proteins in tissue. The salt functional group component of CMC is sensitive to changes in pH. Specifically, as CMC becomes more acidic, a reduction of the salt form is observed as the carboxylate anion (COO—) groups become neutralized by the substitution of a proton (H+). A reduction of the salt form results in decreased CMC water solubility and loss of tissue adherence properties. Thus, maintaining a minimum amount of surface charge on the CMC fixating material or coating material of the hybrid materials is critical to maintaining mucoadhesive performance. In certain embodiments, the fixating layer may be used as a carrier to facilitate the delivery of one or more therapeutic agents.

In accordance with the present invention, by controlling the chemical interactions between the CMC-omega-3 fatty acid materials, the mucoadhesive properties of the fixating material can be altered. Likewise, by controlling the chemical interactions between the CMC-omega-3 fatty acid materials, the abilities of such fixating material to hydrate, to release therapeutic agents contained therein and the bioabsorption properties thereof may be altered or otherwise influenced. For example, when in contact with a fixating material such as CMC, the biomaterial or layer (e.g., an omega-3 fatty acid-based material) facilitates the transfer of protons (H+) to the fixating material. As a result, the surface charge on the fixating material or coating material may be further neutralized, thereby decreasing the water solubility of the fixating material (e.g., CMC) and resulting in a corresponding decrease in the tissue adherence properties of the fixating material. Similarly, neutralization of the surface charge of the fixating material influences the rate at which one or more therapeutic agents are eluted from such fixating material. For example, by decreasing the water solubility of the fixating material (e.g., by coupling the fixating material to a fatty acid-based biomaterial layer) the rate at which a therapeutic agent is released from the fixating layer is reduced, extended and/or delayed.

By increasing the solubility or the rate at which the fixating material and/or the biomaterial layer hydrolyzes, the bioabsorption properties of the materials, layers, films, coatings and gels disclosed herein can be enhanced. Accordingly, in one aspect, the invention provides methods of modulating a bioabsorbability of the materials, layers, films, coatings and gels disclosed herein (e.g., by modulating the rate at which such materials, layers, films, coatings and gel hydrolyze). The invention also provides biomaterial layers, films, coatings and gels which can be prepared according to the methods discussed herein.

In certain embodiments, the fixating layer may be prepared such that it includes one or more plasticizing agents such as glycerol, propylene glycol, poly ethylene glycol, triacetin citrate or triacetin. The addition of a plasticizing agent (e.g., glycerol) to such fixating layer serves to add plasticity to the fixating layer, but can also serve as a vehicle to facilitate proton transfer between the fatty acid-based biomaterial layer and the fixating layer. As a result, the surface charge on the fixating material or coating material may be further neutralized by the presence of a plasticizing agent enabling proton transferal, thereby decreasing the water solubility of the fixating material (e.g., CMC) and resulting in a corresponding decrease in the tissue adherence and therapeutic agent release properties of the fixating material.

While certain compounds, compositions and methods of the present invention have been described with specificity in accordance with certain embodiments, the following examples serve only to illustrate the compounds of the invention and are not intended to limit the same. The articles "a" and "an" as used herein in the specification and in the claims, unless clearly indicated to the contrary, should be understood to include the plural referents. As used herein, the term "about" will be understood by persons of ordinary skill in the art and may vary to some extent on the context in which such term is used. To the extent that there may be uses of the term which are not immediately clear to persons of ordinary skill in the art given the context in which is used, the term "about" will mean up to plus or minus twenty percent of the given term. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

Example 1

Double-layered films of fatty acid-based, biomaterial layers and CMC-based fixating layers were prepared and demonstrated local release of therapeutic agents. The fatty acid-based, biomaterial layers were prepared by oxidatively crosslinking fish oil by exposure of the fatty acids to thermal curing conditions in the presence of oxygen. The CMC-based fixating layer was then prepared with glycerol as a plasticizing agent and cast on top of the fatty acid-based film or layer.

Paclitaxel was selected as a model hydrophobic therapeutic agent and its release kinetics were examined when applied to either the fatty acid-based layer or fixating layer of the film. The fatty acids in the fatty acid based-layer, the CMC in the fixating layer and the paclitaxel were all labeled with specific fluorophores to enable simultaneous tracking of the film's hydrolysis products and drug release, as well to correlate behavior in vitro and in vivo after implantation in the dorsal subcutaneous space of mice as an indication of the bioabsorption of the film in vivo.

To facilitate tracking of the hydrolysis of the constructed double-layered film and therapeutic agent release kinetics in vivo, a noninvasive imaging assay was developed. Specifically, fluorescently labeled NBD-stearate was used as a reporter for fatty acid hydrolysis. This lipid (Avanti Polar Lipids, excitation 500 nm and emission 540 nm) is added to the process and behaves similarly to the other fatty acids that comprise the fatty acid-based, biomaterial. Similarly, the CMC-based fixating layer was labeled with Xenolight 647 (Invitrogen, excitation 640 nm and emission 680 nm). The labeled paclitaxel (excitation 535 nm and emission 580 nm) signal could be differentiated from the fatty acid-based and CMC-based signals. The ability to track the hydrolysis of construct components in vivo along with drug release is critical and enables the correlation between hydrolysis and release, along with the relationships between hydrolysis and drug release in vitro and in vivo, to form predictive models that enable forecasting of in vivo behavior from in vitro profiles. Subcutaneous implantation of the constructed double-layered film demonstrated no adverse tissue response, as expected from such natural materials.

Figure 2:
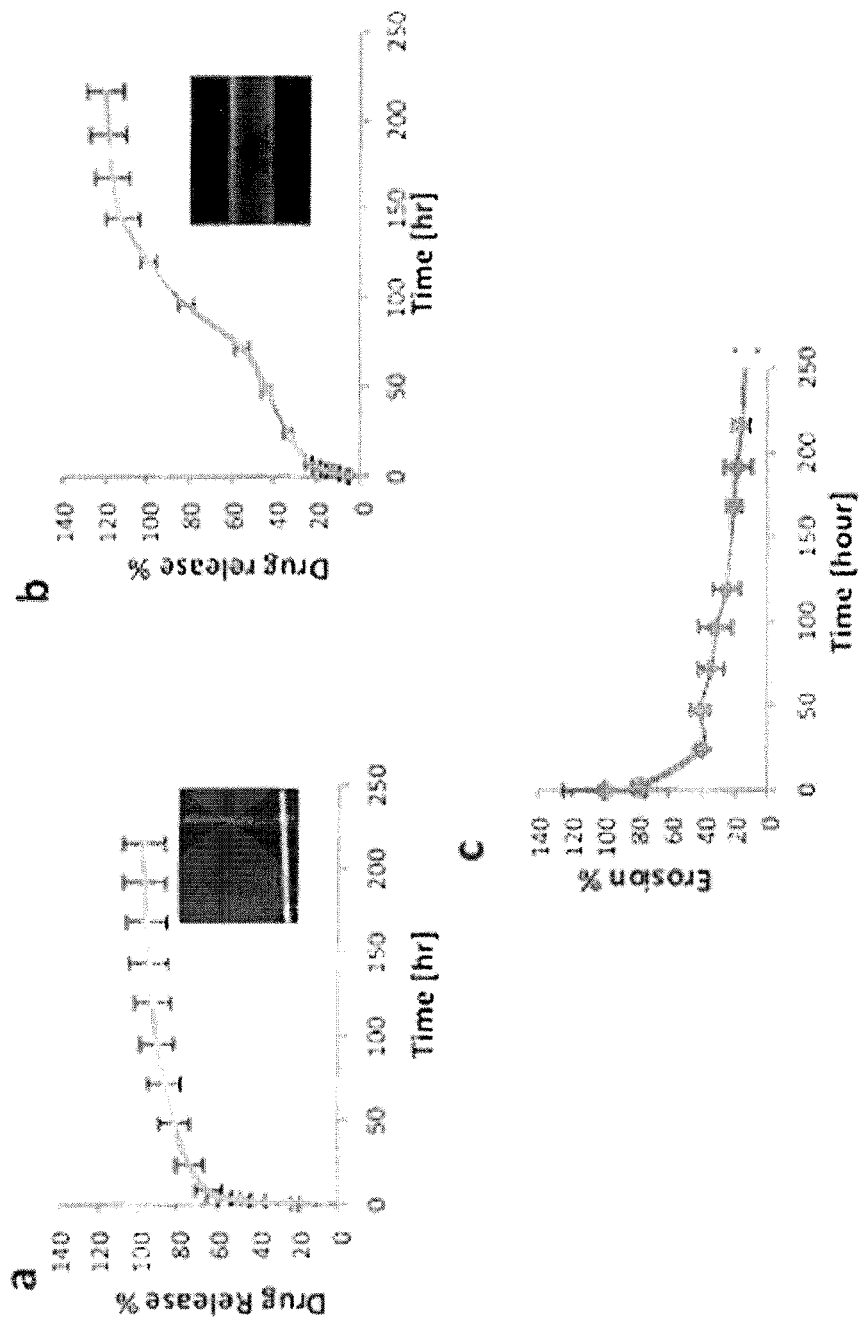
FIGS. 2A, 2B and 2C illustrate film images and the therapeutic agent release profiles from such films.

The therapeutic agent release kinetics observed were dependent on the constituent materials that comprised each of the fatty acid-based, biomaterial layer (FIG. 2B) and the CMC-based fixating layers (FIG. 2A). The therapeutic agent was observed to have penetrated poorly (3 µm) into the CMC-based fixating layer and penetrated deeply into the fatty acid-based, biomaterial layer (65 µm).

Release of the therapeutic agent from each of the fatty acid-based, biomaterial layer and the fixating layer proceeded differentially in vitro and followed the distinct hydrolysis modes of the two constituent layers. We hypothesized that material hydrolysis is the determining factor controlling release kinetics of the therapeutic agent. Release of the therapeutic agents from the prepared film was dependent upon the fatty acid composition of the fatty acid-based, biomaterial layer (FIG. 2A vs. FIG. 2C, linear correlation R=0.99). The prepared film constructs eliminated the diffusivity component of the therapeutic agent and enabled full control over therapeutic agent release profile through manipulation of composition and oxidative conditions to form distinct fatty acid cross-linked networks. Networks of cross-linked fatty acids with a higher number of polar groups (e.g. hydroxyls), were more hydrophilic (as demonstrated by contact angle measurements) and were observed to swell and hydrolyze faster, thereby modulating drug release kinetics.

The foregoing study confirms that oil-based materials show promise as scaffolds for therapeutic agent delivery and release. The study also demonstrates that when the therapeutic agent is applied to the faster hydrolyzing CMC-based fixating material or layer, it results in a faster release profile as compared to when it is incorporated into the more slowly hydrolyzing omega-3 fatty acid-based, biomaterial or layer. Such materials are biocompatible and enable high tunability based on starting fatty acid composition and thermal oxidative processing conditions. Network crosslinking or fatty acid density dictates hydrolysis kinetics that in turn fully controls drug release profile while abrogating drug diffusion.

Example 2

Fatty acid-based, biomaterial films of 0.5 mm and 4.0 mm thickness were prepared and which comprised fish oil triglycerides. Such films also contained a fluorophore (0.3% NBD-12 stearate) to facilitate tracking of the film's hydrolysis. The two films were confirmed to be equivalent chemically via FTIR and fatty acid profile and only differed in thickness and thus in the coating density (mass per unit area). In this study, the 0.5 mm films had an estimated coating density of 13.8 mg/in$^2$ and the 4.0 mm films of 124.0 mg/in$^2$. Each of the films had approximately 25% unbound material prior to the study.

The films were placed in a simulated peritoneal fluid comprised of 37% calf serum and 63% Dulbecco's Modified Eagle Medium (DMEM) and incubated at 37° C. The films were removed and the fluorescence measured by an in viva imaging system (IVIS). The change in fluorescence was used to calculate the amount of material that had been removed from the film. Since the material was in an aqueous buffer, the method of hydrolysis modeled in these experiments is hydrolytic.

Figure 3:
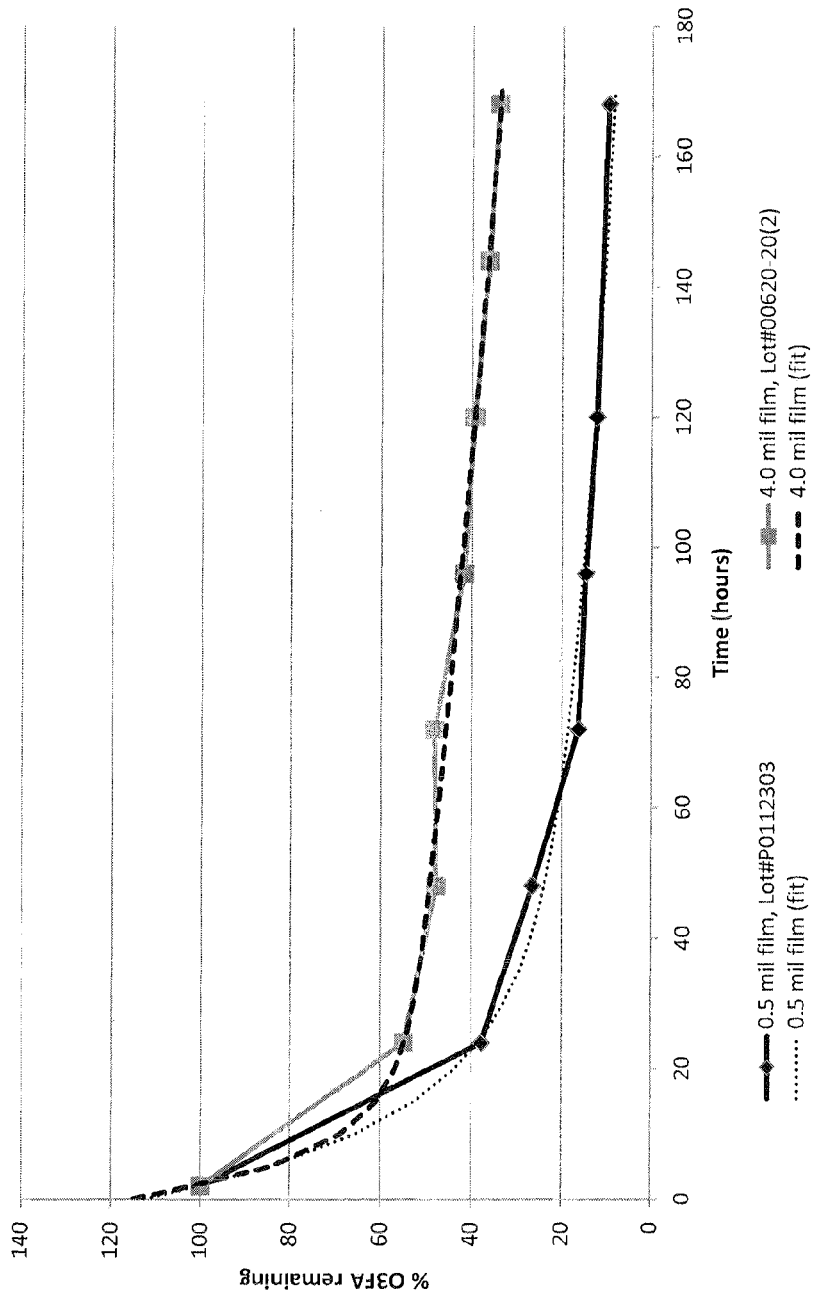
FIG. 3 illustrates that the mass of prepared fatty acid-based biomaterial film materials of different thicknesses (0.5 mm and 4.0 mm) changes as a function of time when exposed to simulated peritoneal fluid.

As illustrated in FIG. 3, the mass of the films changed as a function of time exposed to the simulated peritoneal fluid, with the 0.5 mm film and the 4 mm film having exponential decay equations of $M=32.6e^{-0.0079t}+79.67e^{-0.0806t}$, $r^2=0.9988$ and $M=57.1e^{-0.0031t}+57.8e^{-0.1448t}$, $r^2=0.9986$, respectively.

Example 3

Hybrid hydrogel-cured oil materials consisting of a cured fish oil (omega-3 fatty acid) biomaterial coating, film or material coupled with a mucoadhesive fixating layer (sodium carboxymethylcellulose or CMC and glycerol) layer were constructed. This allows for the CMC-based fixating layer of the resulting hybrid material to adhere to the surface of tissues while the omega-3 fatty acid-based biomaterial layer provides barrier functionality. The glycerol component of the fixating layer serves to add plasticity and may also serve as a vehicle to facilitate proton transfer between the omega-3 fatty acid-based biomaterial layer and the fixating layer.

An important attribute of the mucoadhesive properties of the CMC-based fixating layer in the hybrid construct is the maintaining of the sodium salt form (FIG. 1) so that the negative charge produced after displacement of the sodium upon hydration can couple to the positive charge produced by amino groups of proteins in tissue.

The salt functional group component of the CMC is sensitive to changes in pH. Specifically, as CMC becomes more acidic, a reduction of the salt form is observed as the carboxylate anion ($COO^-$) groups become neutralized by the substitution of a proton ($H^+$). A reduction of the salt form results in decreased CMC water solubility and loss of tissue adherence properties. Thus, maintaining a minimum amount of surface charge on the CMC-based fixating layer of the hybrid construct is critical to maintaining mucoadhesive performance. By controlling the chemical interactions between the CMC-based fixating layer and the omega-3 fatty acid-based biomaterial layer or materials, the mucoadhesive performance of the fixating layer can be altered.

Another aspect of the invention is to use such hybrid coatings prepared using a CMC-based layer and an omega-3 fatty acid-based biomaterial layer or material as a means to control delivery and release of one or more therapeutic agents. Research and development work performed demonstrated that the rate of hydrolysis of such hybrid materials could be extended or decreased in both in-vitro and in-vivo testing by altering the underlying fatty acid chemistry of omega-3 fatty acid biomaterial. Based on these findings and internal product characterization being performed to support the C-QUR Film product development project as further described in U.S. Publication No.: 2010/0183697, the entire teachings of which are incorporated by reference herein, it was decided to expand the possibility of this concept being extended to using hybrid fatty acid-carboxymethylcellulose materials as a means to alter drug release differently from within the same construct.

Example 4

To conduct the instant study, 25 μL of radiolabeled paclitaxel was applied to the omega-3 fatty acid layer of 2 different free-standing films. One film was 0.5 mm of omega-3 fatty acid with the mucoadhesive, CMC-based fixating layer and the other film was 2.0 mm of the omega-3 fatty acid biomaterial layer with no mucoadhesive fixating layer. The concentrations of paclitaxel in the aliquots were 0, 50, 100, and 200 μg/mL, resulting in total mass of paclitaxel applied of 0, 1.25, 2.5, and 5.0 μg. The films were then applied to the lumen of carotid arteries. For the 0.5 mm CMC-based film, the CMC side was adhered to the artery. The samples were incubated in calf serum for 2 hours at 37° C., the films were removed, and the arteries assessed for amount of paclitaxel uptake via scintillation.

Figure 4:
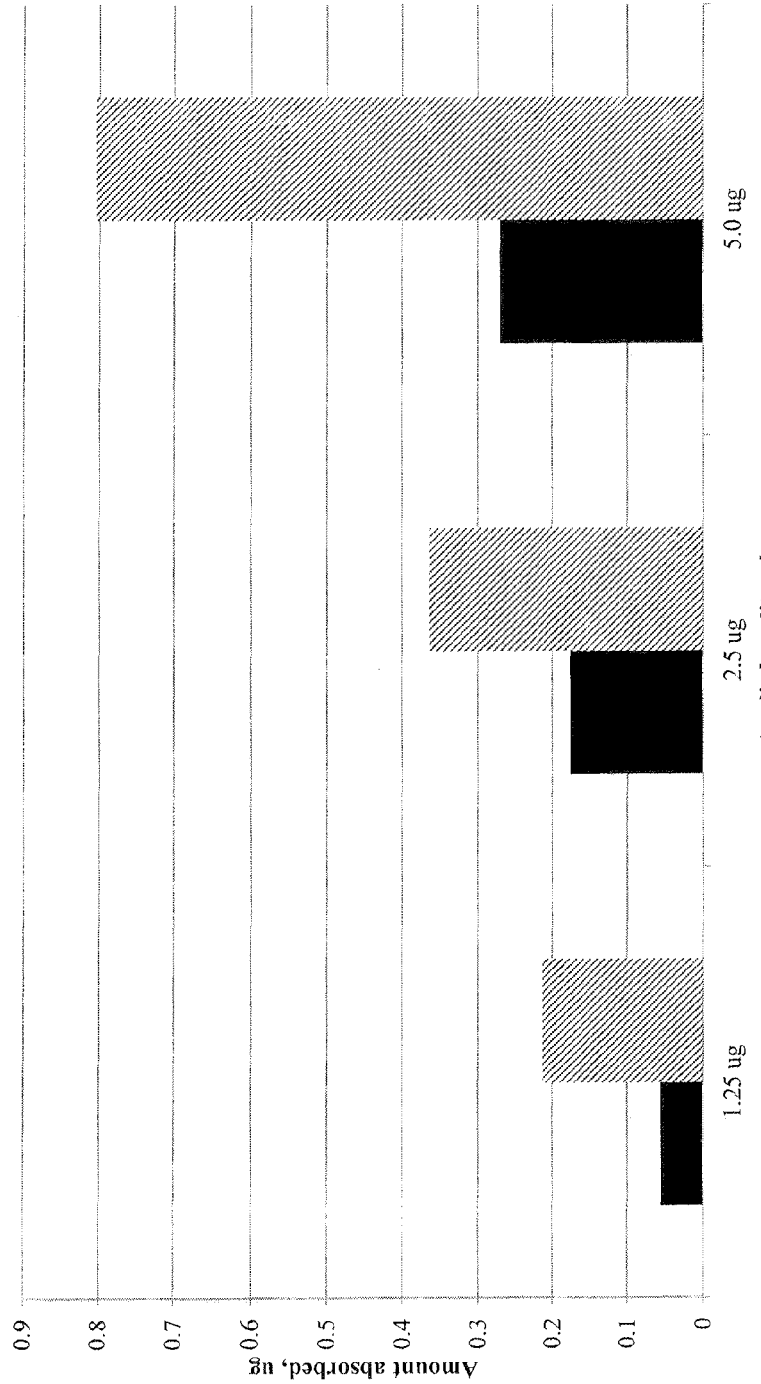
FIG. 4 illustrates the uptake of paclitaxel from different films prepared with and without the use of a CMC-based fixating layer, as measured by scintillation.

The results of the instant study are presented in FIG. 4. As illustrated in FIG. 4, when the therapeutic agent is applied to the faster hydrolyzing CMC-based fixating layer and then subsequently placed in contact with tissue, the faster release profile contributes to greater early tissue uptake. The average percentage of therapeutic agent absorbed by the tissues was 15.9% for the 0.5 mm CMC-based film and 5.7% for the film that did not contain a CMC-based fixating layer, thus supporting the conclusion that by increasing the rate at which the films hydrolyze, such films are rendered more bioabsorbable.

Example 5

In the present study, the ability of the cured fatty acid-based, biomaterial to alter the carboxymethylcellulose sodium salt protonation state (i.e. charge state) was investigated. For this experiment samples were packaged at a high (45% RH) and a low (10% RH) humidity for both 1.5 mm and 5.0 mm films, each of which comprised both a CMC-based fixating layer and a fatty acid-based, biomaterial layer (i.e., for the 1.5 mm film, the CMC-based layer being approximately 1 mm and the fatty acid-based, biomaterial layer being the balance). The films were packaged, sterilized and then subjected to heating at 45° C. at different time points to accelerate proton transfer from the fatty acid-based layer to the CMC carboxyl sodium salts that comprise the fixating layer.

Figure 5A:
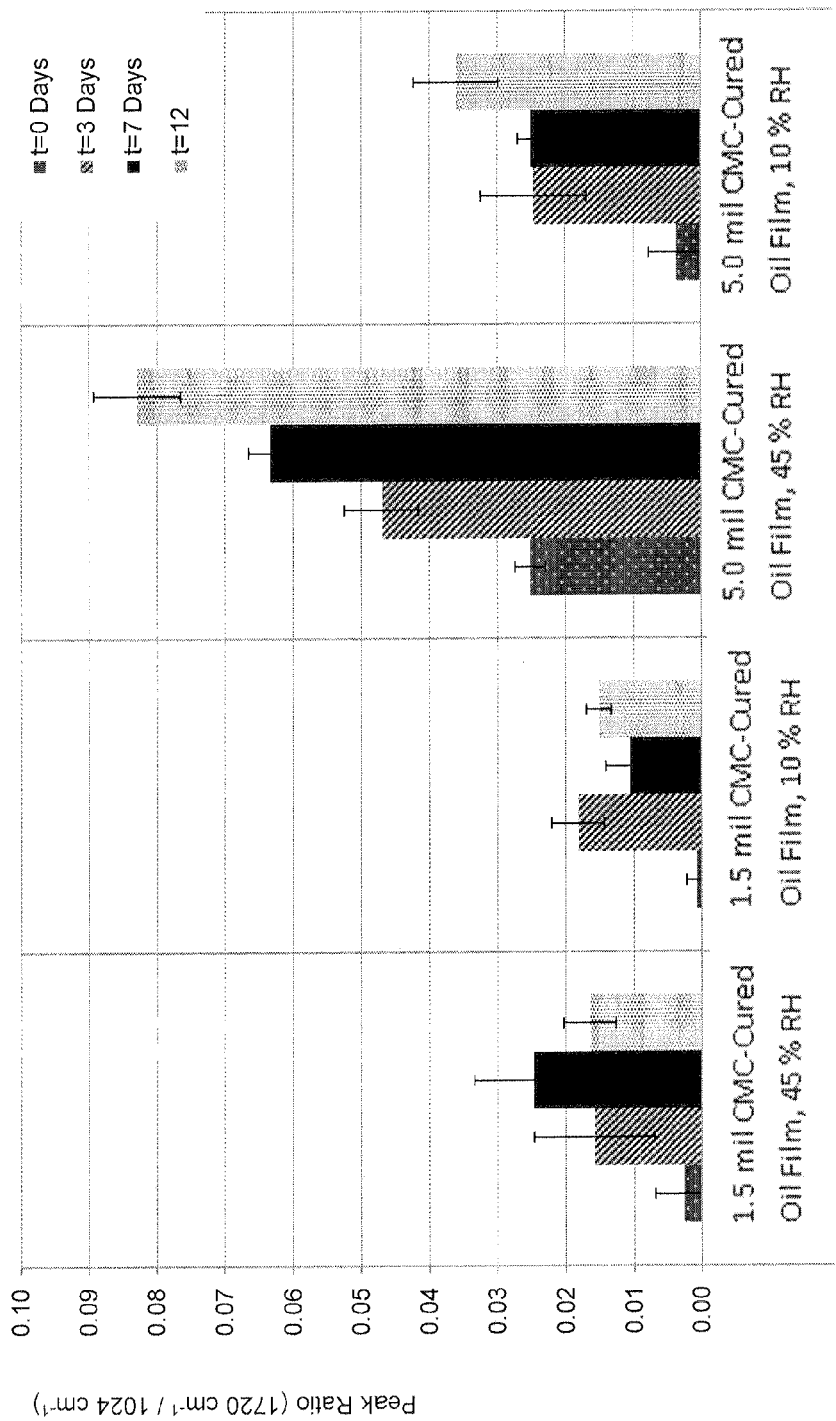
FIG. 5A illustrates the effects of packaging humidity on the films prepared using a CMC-based fixating layer and a fatty acid-based biomaterial layer (FTIR Protonation Peak Ratio: 1720 $cm^{-1}$/1024 $cm^{-1}$).
Figure 5B:
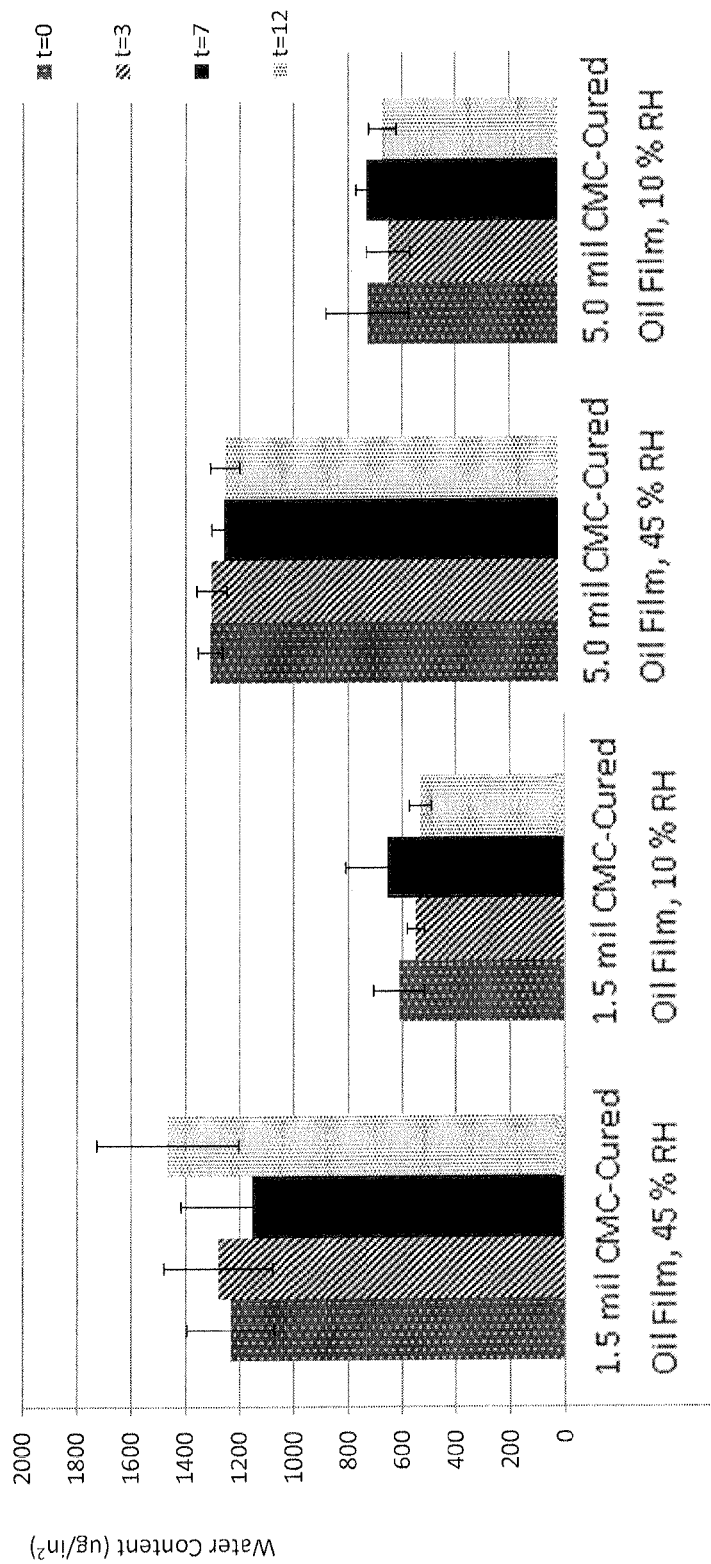
FIG. 5B illustrates the measured water content of sealed packages throughout accelerated aging of the films prepared using a CMC-based fixating layer and a fatty acid-based biomaterial layer.

The results of this experiment demonstrated that the amount of the cured oil fatty acid component (i.e., acidic environment and proton source) and humidity level (affecting film water content to facilitate proton transfer) directly impacted the ability for the CMC to become protonated, as depicted in FIGS. 5A and 5B.

The forgoing studies confirm that the films prepared using a CMC-based fixating layer and a fatty acid-based, biomaterial layer are unexpected and unique where they are not just extruded layers that are laminated together. Rather, a chemical interaction exists between the fixating layer and the biomaterial layer which can be harnessed to control drug delivery. In particular, the foregoing provides evidence that the aqueous solubility and tissue adherence of carboxymethylcellulose (CMC) is dependent on the anionic (i.e. charged) state of the polymer that comprises the fixating layer, and furthermore that a decrease in CMC hydrophilicity due to a decrease in anionic content is a result of proton (H+) addition to the charged functional groups. Accordingly, the fatty acid-based, biomaterial layer can serve as a proton reservoir, whereas the residual water content and mass of fatty acids in the material can influence the protonation rate of the carboxymethylcellulose in the fixating layer. By altering the protonation rate and aqueous solubility of the carboxymethylcellulose, the release of therapeutic agents can be controlled and tailored.

In another aspect of this invention, the protonation rate of the carboxymethylcellulose can be additionally altered by changing the starting fatty acid composition and hydrolysis rate of the cured oil material. Layers of drug release reservoirs can be created where a fixating layer can be applied onto the biomaterial layer or coating of varying fatty acid compositions. Alternatively, layers of alternating fixating layers and biomaterial layers can be used in order to control different drug release rates from a hybrid material. Furthermore, the hydrolysis rate of the biomaterial layer can be controlled by altering starting oil and/or fatty acid chemistry and/or the cured material density and surface area. Similarly, the charge of the fixating layer can be altered by using polymers of different starting levels of ionic substitution, or by using different cured oil fatty acid chemistries (proton sources). Additionally, in one aspect of this invention, the charge and/or cross-linking of the fixating material or layer can be manipulated by the presence of monovalent, divalent, or polyvalent cations.

The present studies also provide that the initial water content of the films prepared using a CMC-based fixating layer and a fatty acid-based, biomaterial layer upon storage can influence material performance. Similarly, temperature is an important aspect of facilitating proton transfer between the CMC-based fixating layer and a fatty acid-based, biomaterial layer and generally, reduced temperature hinders proton transfer where elevated temperature accelerates proton transfer. The use of, for example, antioxidants (e.g., vitamin C) can be used as a free radical scavenger as a means to control the hydrolysis of one or more of the CMC-based fixating layer, the fatty acid-based, biomaterial layer, and/or the therapeutic during sterilization and material storage. Additionally, the antioxidant can be used as a plasticizer. Additional polar materials (e.g., glycerol, monoglycerides, or free fatty acids) can be added to modulate the plasticity of the films prepared using a CMC-based fixating layer and a fatty acid-based and/or facilitate proton transfer between fatty acid and hydrogel components.

While the foregoing examples are directed to the use of Na—CMC, it should be understood that the concepts and findings presented herein are generally applicable to other fixating materials and/or biomaterial. In certain embodiments, such fixating materials contain ionically charged functional groups.

Example 6

Three different coatings were prepared with different types of fatty acid materials. These coatings were (1) fish oil, (2) fish oil enriched with fish oil ethyl esters, and (3) flaxseed oil. Fluorescently labeled paclitaxel, a hydrophobic drug, dissolved in ethanol was pipetted onto the surface of the coating. These samples were incubated at 37° C. in a media consisting of 37% calf serum and 63% DMEM (Dulbecco's Minimum Eagle Medium) and the amount of drug eluted from the surface as a function of time was determined by fluorescent measurements taken by an in vivo imaging system (IVIS).

Figure 6A:
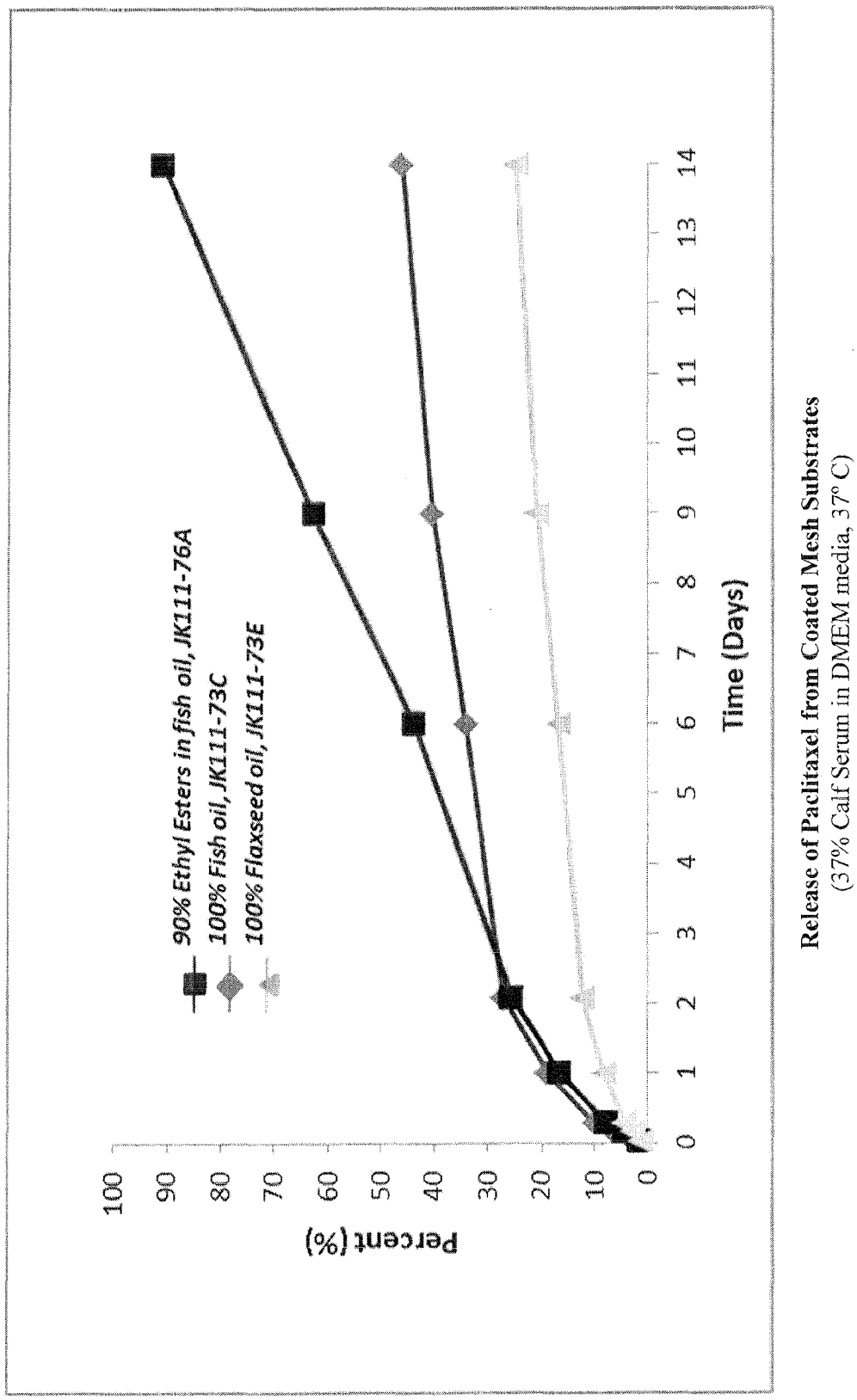
FIG. 6A illustrates the release of paclitaxel from coating materials prepared from fish oil, a blended mixture of fish oil and fish oil ethyl esters, or flaxseed oil.

By changing the type of coating material, different drug release profiles were obtained. Oils that were more hydrophilic released the drug more quickly in aqueous media than oils that were more hydrophobic, as illustrated in FIG. 6A.

Figure 6B:
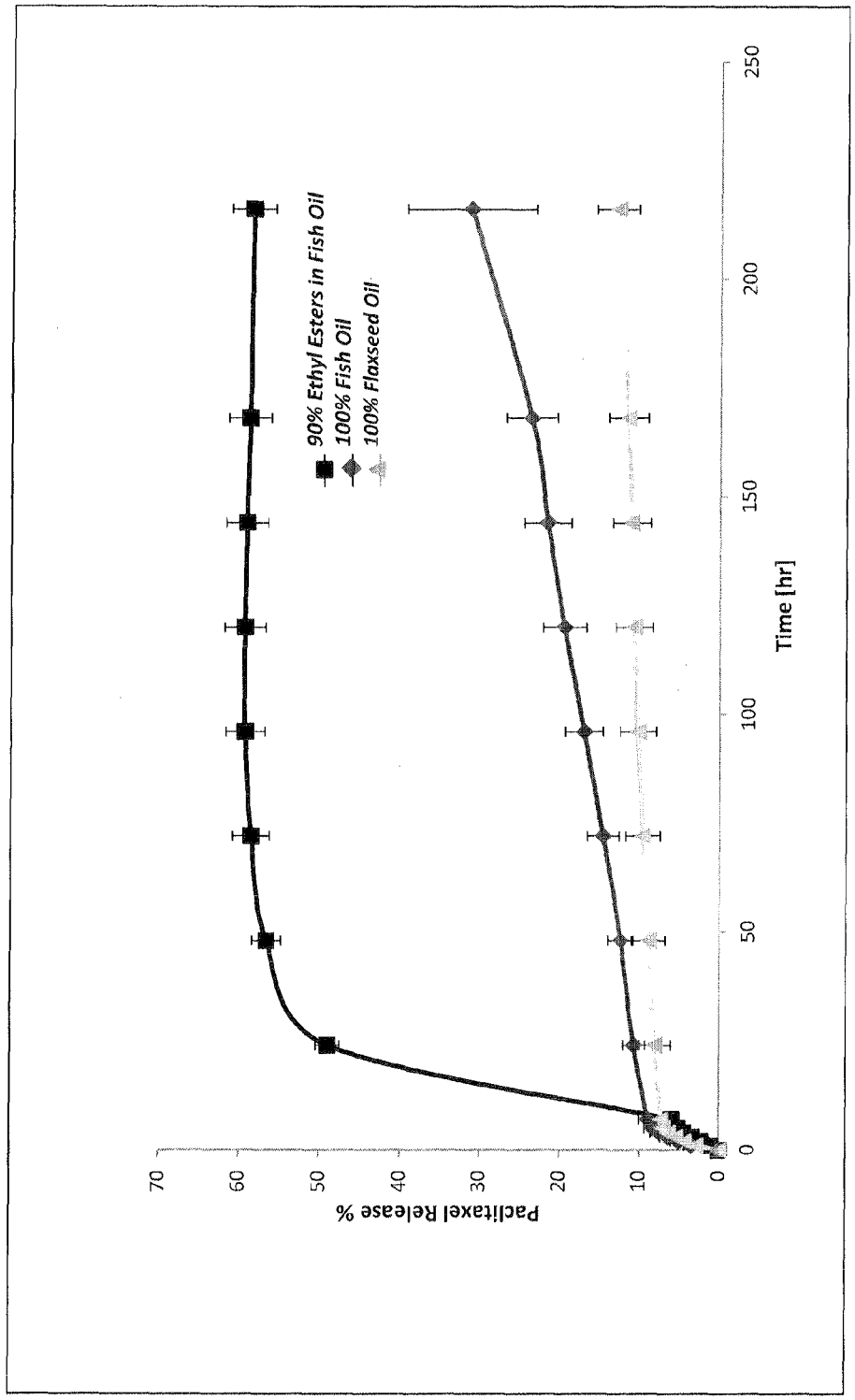
FIG. 6B illustrates the release of triclosan from coating materials prepared from fish oil, a blended mixture of fish oil and fish oil ethyl esters, or flaxseed oil.

These coatings were similarly coated with triclosan, a hydrophilic drug, and incubated in pH 7 PBS buffer at 37° C. and the amount of drug eluted from the surface as a function of time was determined by HPLC assay. As illustrated in FIG. 6B, the oils that were more hydrophilic released the drug more quickly in aqueous media than oils that were more hydrophobic.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A coating material coating a medical device, comprising:
   a biomaterial layer comprising a biomaterial, wherein the biomaterial comprises fatty acids cross-linked to each other; and
   a fixating material layer comprising a fixating material, wherein the fixating material comprises material selected from the group consisting of sodium carboxymethylcellulose (Na—CMC), poly(ethylene glycol), poly(ethylene oxide), poly(HEMA), poly(N-vinyl pyrrolidone), poly(acrylic acid), carboxymethyl cellulose (CMC), and chitosan, and wherein the fixating material layer is disposed on an outer surface of the biomaterial layer relative to the medical device, and the biomaterial protonates the fixating material so as to alter a drug eluting property of the fixating material;
   wherein the fixating material layer comprises one or more therapeutic agents; and
   wherein the coating material effects controlled delivery in a patient of the one or more therapeutic agents from the coating material based on at least the altered drug eluting property of the fixating material.

2. The coating material of claim 1, wherein the biomaterial layer comprises one or more therapeutic agents and wherein the rate of release of the one or more therapeutic agents from the fixating material layer is extended at least in part by the protonation of the fixating material caused by a relative amount of fatty acids in the biomaterial.

3. The coating material of claim 1, wherein the biomaterial layer comprises a first therapeutic agent, wherein the fixating material layer comprises a second therapeutic agent, wherein the biomaterial layer releases the first therapeutic agent at a first rate, and wherein the fixating material layer releases the second therapeutic agent at a second rate.

4. The coating material of claim 3, wherein the second rate is influenced by a composition of the biomaterial.

5. The coating material of claim 3, wherein the biomaterial has a high fatty acid density and wherein the high fatty acid density delays the second rate.

6. The coating material of claim 3, wherein the biomaterial has a low fatty acid density of about 13.8 mg/in$^2$ and wherein the low fatty acid density accelerates the second rate.

7. The coating material of claim 2, wherein the fixating material is sodium carboxymethylcellulose (Na—CMC).

8. The coating material of claim 1, wherein the biomaterial further comprises alpha-tocopherol.

9. The coating material of claim 1, wherein the biomaterial further comprises fish oil.

10. The coating material of claim 1, wherein the fatty acids are omega-3 fatty acids.

11. The coating material of claim 1, wherein the fatty acids are selected from the group consisting of eicosapentaenoic acid (EPA) and docosahexaenoic acid (DHA), and combinations thereof.

12. The coating material of claim 1, wherein the coating is on the medical device.

13. The coating material of claim 12, wherein the medical device is selected from the group consisting of a surgical mesh, a graft, a catheter balloon, a stand-alone film and a stent.

14. The coating material of claim 1, further comprising a plasticizing agent.

15. The coating material of claim 14, wherein the plasticizing agent is selected from the group consisting of glycerin, propylene glycol, poly ethylene glycol, triacetin citrate, triacetin and combinations thereof.

16. The coating material of claim 1, wherein the coating material is bioabsorbable.

17. The coating material of claim 1, wherein the fixating material fixates the coating material to tissue in vivo for a duration of greater than 10 days.

18. The coating material of claim 1, wherein the fixating material layer comprises one or more therapeutic agents and wherein the one or more therapeutic agents is released from the fixating material layer for a duration of greater than 10 days.

19. The coating material of claim 1, wherein the biomaterial further comprises ethyl esters of one or more fatty acids selected from the group consisting of eicosapentaenoic acid (EPA) and docosahexaenoic acid (DHA).

20. A film, comprising:
   a biomaterial, wherein the biomaterial comprises fatty acids cross-linked to each other; and
   a fixating material, wherein the fixating material is disposed as a layer on an outer surface of the biomaterial, and the biomaterial protonates the fixating material so as to alter a drug eluting property of the fixating material;
   wherein the fixating material comprises sodium carboxymethylcellulose and one or more therapeutic agents; and
   wherein the film is implantable in a patient to effect controlled delivery of the one or more therapeutic agents to the patient based on at least the altered drug eluting property of the fixating material.

21. The film of claim 20, wherein the biomaterial comprises the one or more therapeutic agents and wherein the rate of release of the one or more therapeutic agents from the fixating material is extended at least in part by the protonation of the fixating material caused by a relative amount of fatty acids in the biomaterial.

22. A film, comprising:
   a biomaterial, wherein the biomaterial comprises fatty acids cross-linked to each other; and
   a fixating material, wherein the fixating material is disposed as a layer on an outer surface of the biomaterial, and the biomaterial protonates the fixating material so as to alter a drug eluting property of the fixating material;
   wherein the fixating material is sodium carboxymethylcellulose; and
   one or more therapeutic agents carried by the biomaterial, or carried by the fixating material, or carried by both the biomaterial and the fixating material;
   wherein the film is implantable in a patient to effect controlled delivery of the one or more therapeutic agents to the patient based on at least the altered drug eluting property of the fixating material.

23. The film of claim 22, wherein the protonation of the fixating material alters water solubility of the fixating material so as to extend delivery of the one or more therapeutic agents from the film.

* * * * *